(12) United States Patent
Sommer et al.

(10) Patent No.: US 11,213,533 B2
(45) Date of Patent: Jan. 4, 2022

(54) COMBINATIONS COMPRISING DIBROMOPROPAMIDINE OR DIMINAZENE AND A TETRACYCLINE ANTI-BACTERIAL AGENT

(71) Applicant: UNION therapeutics A/S, Hellerup (DK)

(72) Inventors: Morten Otto Alexander Sommer, Hellerup (DK); Rasmus Toft-Kehler, Hellerup (DK)

(73) Assignee: UNION Therapeutics A/S, Hellerup (DK)

( * ) Notice: Subject to any disclaimer, the term of this patent is extended or adjusted under 35 U.S.C. 154(b) by 0 days.

(21) Appl. No.: 16/330,502

(22) PCT Filed: Sep. 14, 2017

(86) PCT No.: PCT/GB2017/052720
§ 371 (c)(1),
(2) Date: Mar. 5, 2019

(87) PCT Pub. No.: WO2018/051102
PCT Pub. Date: Mar. 22, 2018

(65) Prior Publication Data
US 2019/0201422 A1    Jul. 4, 2019

(30) Foreign Application Priority Data
Sep. 15, 2016  (GB) ..................... 1615693

(51) Int. Cl.
| A61K 31/655 | (2006.01) |
| A61K 31/155 | (2006.01) |
| A61K 31/65  | (2006.01) |
| A61P 31/04  | (2006.01) |
| A61K 9/00   | (2006.01) |
| A61K 31/55  | (2006.01) |

(52) U.S. Cl.
CPC ............ *A61K 31/655* (2013.01); *A61K 9/007* (2013.01); *A61K 9/0014* (2013.01); *A61K 31/155* (2013.01); *A61K 31/65* (2013.01); *A61P 31/04* (2018.01); *A61K 31/55* (2013.01); *Y02A 50/30* (2018.01)

(58) Field of Classification Search
CPC ................................ A61K 31/55; A61K 31/65
USPC ................................................. 514/637, 634
See application file for complete search history.

(56) References Cited

U.S. PATENT DOCUMENTS

| 5,204,113 | A  | 4/1993  | Hartley et al. |
| 5,230,897 | A  | 7/1993  | Griffin et al. |
| 6,346,391 | B1 | 2/2002  | Oethinger et al. |
| 6,552,363 | B2 | 4/2003  | Sridevan |
| 6,677,133 | B2 | 1/2004  | Oethinger et al. |
| 7,026,136 | B2 | 4/2006  | Oethinger et al. |
| 7,879,795 | B2 | 2/2011  | Glinka et al. |
| 7,947,741 | B2 | 5/2011  | Bostian et al. |
| 7,994,225 | B2 | 8/2011  | Bostian et al. |
| 8,012,711 | B2 | 9/2011  | Oethinger et al. |
| 8,871,184 | B2 | 10/2014 | Tamarkin et al. |
| 8,992,896 | B2 | 3/2015  | Tamarkin et al. |
| 9,949,988 | B2 | 4/2018  | Delavenne et al. |
| 10,463,680 | B2 | 11/2019 | Sommer et al. |
| 10,758,553 | B2 | 9/2020  | Delavenne et al. |
| 10,857,164 | B2 | 12/2020 | Sommer et al. |
| 2006/0264517 | A1 | 11/2006 | Oethinger et al. |
| 2008/0132457 | A1 | 6/2008  | Bostian et al. |
| 2008/0188445 | A1 | 8/2008  | Muldoon et al. |
| 2009/0253660 | A1 | 10/2009 | Johnston |
| 2014/0348787 | A1 | 11/2014 | Simmons |
| 2016/0051686 | A1 | 2/2016  | Simmons et al. |
| 2019/0151231 | A1 | 5/2019  | Sommer et al. |
| 2020/0268693 | A1 | 8/2020  | Mylonakis et al. |
| 2020/0306269 | A1 | 10/2020 | Delavenne et al. |
| 2020/0306270 | A1 | 10/2020 | Delavenne et al. |
| 2020/0306271 | A1 | 10/2020 | Delavenne et al. |

FOREIGN PATENT DOCUMENTS

| BR | 0304738 A      | 5/2005  |
| EP | 125858         | 11/1984 |
| EP | 439450         | 8/1991  |
| EP | 1276503        | 1/2003  |
| EP | 1285579        | 2/2003  |
| EP | 1674112        | 6/2006  |
| EP | 2046732        | 4/2009  |
| EP | 2987784        | 2/2016  |
| GB | 2212394 A      | 7/1989  |
| WO | WO 2003/075857 A2 | 9/2003 |
| WO | WO-2005/089738 | 9/2005  |
| WO | WO-2008/079339 | 7/2008  |
| WO | WO-2009/098595 | 8/2009  |

(Continued)

OTHER PUBLICATIONS

Gonde, et al., A unique case of *Babesia gibsoni* infected dog with paraplegia, J. Parasit. Dis., Jan. 13, 2016, pp. 1605-1608, vol. 40, No. 4.

(Continued)

*Primary Examiner* — Kevin E Weddington
(74) *Attorney, Agent, or Firm* — Mintz, Levin, Cohn, Ferris, Glovsky and Popeo, P.C.

(57) ABSTRACT

This invention relates to combination products comprising an amidine selected from dibromopropamidine and diminazene or a pharmaceutically acceptable salt or solvate thereof; and a tetracycline anti-bacterial agent. The combination products are suitable for use in the treatment of bacterial infections or diseases.

15 Claims, 1 Drawing Sheet

(56) References Cited

FOREIGN PATENT DOCUMENTS

| WO | WO-2009/111064 | 9/2009 |
| WO | 2016193136 | 12/2016 |
| WO | 2019192968 | 10/2019 |
| WO | 2020176067 | 9/2020 |

OTHER PUBLICATIONS

European Patent Office, International Search Report and Written Opinion for PCT International Patent Application No. PCT/GB2017/052720, dated Nov. 22, 2017, 11 pages.
Alsaimary et al., "Bacterial wound infections in diabetic patients and their therapeutic implications," Medical Practice and Review, 1(2), pp. 12-15 (2010).
Champion and McDowall, Clinical observations on the use of dibromopropamidine (M & B 1270) for surface infections, with particular reference to B. Proteus Vulgaris and PS. Pyocyanea, British Journal of Plastic Surgery, 2(1), pp. 57-60 (1949).
Donkor and Clark, "In vitro antimicrobial activity of aromatic diamidines and diimidazolines related to pentamidinie," Eur. J. Med. Chem., 34, pp. 639-643 (1999).
Høiby et al., "*Pseudomonas aeruginosa* biofilms in cystic fibrosis," Future Microbiol., 5(11), pp. 1663-1674 (2010).
Jennings, "Effect of tetracycline administration on the efficacy of diminazene aceturate therapy and prophylaxis in *Trypanosoma brucei* infections of mice," Research in Veterinary Science, 43, pp. 173-176 (1987).
Kaatz, "Inhibition of bacterial efflux pumps: a new strategy to combat increasing antimicrobial agent resistance," Expert Opinion on Emerging Drugs, 7(2), pp. 223-233 (2002).
Libman et al., "Antistaphylococcal Activity of Pentamidine," Antimicr. Agents and Chemother., 34(9) pp. 1795-1796 (1990).
Lin and Huang, "Use of doxycycline-enroflaxacin-metronidazole combination with/without diminazene diaceturate to treat naturally occuring canine babesiosis caused by *Babesia gibsoni*," Acta Veterinaria Scandinavica, 52(27), 4 pages (2010).
Lomovskaya et al., "Identification and Characterization of Inhibitors of Multidrug Resistance Efflux Pumps in Pseudomonas aeruginosa: Novel Agents for Combinaiton Therapy," Antimicrobial Agents and Chemotherapy, 45(1), pp. 105-116 (2001).
Mitchell et al., "QacA Multidrug Efflux Pump from *Staphylococcus aureus*: Comparative Analysis of Resistance to Diamidines, Biguanidines, and Guanylhydrazones," Antimicrobial Agents and Chemotherapy, 42(2), pp. 475-477 (1998).
Mouton et al., "Conserving antibiotics for the future: New ways to use old and new drugs from a pharmacokinetic and pharmacodynamic perspective," Drug Resistance Updates, 14, pp. 107-117 (2011).
Peregrine and Mamman, "Pharmacology of diminazene: a review," Acta Tropica, 54, pp. 185-203 (1993).
Woodside, "Studies on the mode of action of dibromopropamidine," Microbios., 8(29), pp. 23-33 (1973).
Rahal Novel Antibiotic Combinations against Infections with Almost Completely Resistant Pseudomonas aeruginosa and Acinetobacter Species, Antibiotic Combinations for Resistant Bacteria, 43(Suppl 2), pp. S95-S99 (2006).
Renau et al., "Conformationally-Restricted Analogues of Efflux Pump Inhibitors that Potentiate the Activity of Levofloxacin in Pseudomonas aeruginos," Bioorg. & Med. Chem. Lett., 13, pp. 2755-2758 (2003).
Richards and Xing, "Evaluation of synergistic effects of combinations of antibacterials having relevance to treatment of burn wound infections," International Journal of Pharmaceutics, 75, pp. 81-88 (1991).
Richards and Xing, "Investigation of Synergism with Combinations of Dibromopropamidine Isethionate or Propamidine Isethionate and Polymyxin B," J. Pharm. Pharmacol., 46, pp. 563-566 (1994).
Richards et al., "An evaluation of the Antibacterial Activities of Combinations of Sulfonamides, Trimethoprim, Dibromopropamidine, and Silver Nitrate Compared with Their Uptakes by Selected Bacteria," J. Pharm. Sci., 80(9), pp. 861-867 (1991).
Richards et al., "Investigation of Cell Envelope Damage to Pseudomonas aeruginosa and Enterobacter cloacae by Dibromopropamidine Isethionate," Journal of Pharmaceutical Sciences, 82(9), pp. 975-977 (1993).
Santos Costa et al., "Multidrug Efflux Pump in *Staphylococcus aureus*: an Update," The Open Microbiology Journal, 7(Suppl 1-M5), pp. 59-71 (2013).
Sohl and Alhajhusain, "Update on the treatment of Pseudomonas aeruginosa pneumonia," Journal of Antimicrobial Chemotherapy, 64, pp. 229-238 (2009).
Suller and Russell, "Antibiotic and biocide resistance in methicillin-resistant *Staphylococcus aureus* and vancomycin-resistant enterococcus," J. Hosp. Infect., 43, pp. 281-291 (1999).
Titcomb, "Topical ocular antibiotics: part 1. Eye disorders," The Pharmaceutical Journal, 264(7084), pp. 298-301 (2000).
Vourli et al., "In vitro interactions of tigecycline-pentamidine combination against multidrug-resistant (MDR) Pseudomonas aeruginosa clinical isolates," European Congress of Clinical Microbiology & Infectious Diseases 2013 (ECCMID 2013), Abstract No. R2612, 1 page (2013).

|  | Tetracycline antibiotics (µg/ml) | | | | | | | | | | | |
|---|---|---|---|---|---|---|---|---|---|---|---|---|
|  | 16 | 8 | 4 | 2 | 1 | 0.5 | 0.25 | 0.125 | 0.0625 | 0.0313 | 0 |  |
|  | 1 | 2 | 3 | 4 | 5 | 6 | 7 | 8 | 9 | 10 | 11 | 12 |
| Diminazene (µg/ml) | | | | | | | | | | | | |
| 10 | A | | | | | | | | | | | +ve ctrl |
| 5.00 | B | | | | | | | | | | | +ve ctrl |
| 2.50 | C | | | | | | | | | | | +ve ctrl |
| 1.25 | D | | | | | | | | | | | +ve ctrl |
| 0.63 | E | | | | | | | | | | | -ve ctrl |
| 0.31 | F | | | | | | | | | | | -ve ctrl |
| 0.16 | G | | | | | | | | | | | -ve ctrl |
| 0 | H | | | | | | | | | | | -ve ctrl |

COMBINATIONS COMPRISING DIBROMOPROPAMIDINE OR DIMINAZENE AND A TETRACYCLINE ANTI-BACTERIAL AGENT

FIELD OF THE INVENTION

This invention relates to combination products comprising (i) an amidine selected from dibromopropamidine and diminazene, or a pharmaceutically acceptable salt or solvate thereof; and (ii) a tetracycline anti-bacterial agent; to the combination products for use in the treatment of bacterial infections or diseases, for example diseases or infections caused by Gram-negative bacteria; and to kits comprising the combination products.

BACKGROUND

The increasing prevalence of infections caused by multidrug-resistant bacteria is a global health problem that has escalated in recent years. Drug-resistant bacterial infections result in considerable patient mortality and morbidity. The number of new antibiotics introduced into clinical practice over the past two decades is limited. Furthermore, bacteria invariably develop resistance to newly introduced therapies and clinically significant resistance can appear in a period of just months to years following introduction of a new antibiotic into clinic. As an example, the emergence of bacterial resistance to tetracyclines, a broad class of antibiotics, has led to a decline in their use against infectious diseases. Due to the development of resistance tetracyclines are no longer used in the treatment of many conditions where they were once the drugs of choice (J. W. Mouton et al. "Conserving antibiotics for the future: New ways to use old and new drugs from a pharmacokinetic and pharmacodynamic perspective", Drug Resistance Updates, 14 (2011), 107-117). Alternative approaches to controlling bacterial infections are therefore urgently needed.

Common bacterial pathogens include aerobic Gram-negative bacilli, such as *Pseudomonas aeruginosa, Escherichia coli, Klebsiella pneumoniae*, and *Acinetobacter* species. Infections due to Gram-positive cocci, such as *Staphylococcus aureus*, particularly methicillin-resistant *S. aureus* (MRSA), have been rapidly emerging in the United States. *Acinetobacter baumannii* is a major cause of nosocomial infections in many hospitals and appears to have a propensity for developing multiple antimicrobial resistance rapidly.

*Pseudomonas aeruginosa* is an opportunistic pathogen to humans, which becomes virulent in many hospital-acquired contaminations. *P. aeruginosa* is the most common multidrug-resistant Gram-negative pathogen causing pneumonia in hospitalized patients. The use of combination therapy is thought to minimize the emergence of resistance and to increase the likelihood of therapeutic success through antimicrobial synergy. The use of combination therapies for *P. aeruginosa* pneumonia has been a long-advocated practice, but the potential increased value of combination therapy over monotherapy remains controversial (J. Antimicrobial Chemotherapy, 64 (2009), 229-238).

Respiratory tract infection with eventual respiratory failure is the major cause of morbidity and mortality in cystic fibrosis (CF). Infective exacerbations need to be treated promptly and effectively to minimize potentially accelerated attrition of lung function. The choice of antibiotic depends on in vitro sensitivity patterns. However, physicians treating patients with CF are increasingly faced with infection with multidrug-resistant bacteria.

CF patients are predisposed to chronic infections caused by a variety of bacteria including *Pseudomonas aeruginosa, Staphylococcus aureus, Haemophilus influenzae, Stenotrophomonas maltophilia, Achromobacter xylosoxidans* and *Burkholderia cepacia* (Bcc), *Streptococcus pneumoniae* and enteric Gram-negative bacteria. *P. aeruginosa* is clinically resistant to many antibiotics including minocycline. *Pseudomonas* and some other Gram-negative bacteria have highly effective drug efflux mechanisms which are often associated with multiple drug resistance and are a major problem in CF patients colonised with strains such as Bcc.

Although much has been achieved in the treatment of CF infections, there is an ongoing need for new antibiotic therapies.

More generally, bacterial resistance to antibiotics is increasing in both community and hospital settings. The Infectious Diseases Society of America (IDSA) has identified that the so called ESKAPE pathogens, *Enterococcus faecium, Staphylococcus aureus, Klebsiella pneumoniae, Acinetobacter baumanii, Pseudomonas aeruginosa*, and enterobacteriaceae, pose particular risks, especially in relation to nosocomial infections.

New antimicrobial agents, for example fifth generation cephalosporins, carbapenems, monobactams, β-lactamase inhibitors, aminoglycosides, quinolones, oxazolidones, glycopeptides and tetracyclines are active against Gram-positive pathogens, like vancomycin-resistant *S. aureus* (VRSA) and MRSA, penicillin-resistant streptococci and vancomycin resistant *Enterococcus* (VRE). However, there are limited new drugs which are active against highly resistant Gram-negative organisms.

The lack of novel antibiotics that are effective against Gram-negative bacteria is a significant problem. Gram-negative bacteria are intrinsically insensitive to a number of antibiotic classes despite possessing the targets upon which these antibiotics act; examples include the macrolides and aminocoumarins. This is predominantly a result of the low permeability of the outer membrane of Gram-negative bacteria. One novel approach to circumvent this lack of antibiotics that are active against Gram-negative bacteria is the identification of adjuvant molecules that potentiate the effects of Gram-positive active antibiotics against Gram-negative bacteria.

The development of a wound infection is a serious complication for patients with diabetes. If a wound infection occurs, it is difficult to treat since the clinical course of the infection is more fulminant and severe, and possess a greater threat to the glycaemic status of the patient. It has been found that wounds are highly infected by aerobic and anaerobic bacterial types; *Propionibacterium granulosum*, an anaerobic bacteria, is a predominant pathogen in diabetic wound infections. *Pseudomonas aeruginosa*, on the other hand, is predominant in non-diabetic wounds (Medical Practice and Review, Vol. 1(2), pp. 12-15, June 2010). In general, diabetic wounds can be infected by any type of bacteria, including *Staphylococcus aureus* and *S. epidermidis*; various species of the genus *Streptococcus*, including *S. pyogenes* and *S. pneumoniae; Escherichia coli*; various species of *Klebsiella*, including *K. pneumoniae*; various species of *Enterobacter, Enterococcus* and Acenitobacter.

It is increasingly recognized that infecting pathogens can enter a biofilm state in which complicates antibiotic treatment (Høiby et al, Future Microbiol. 2010, November; 5(11): 1663-74). Biofilms are believed to be relevant in various types of infections including chronic lung infections, wound infections and infections related to indwelling catheters. There is thus a requirement for combination products to treat infections or diseases in a biofilm.

Dibromopropamidine is an amidine compound which has known uses as an antimicrobial agent and disinfectant. It is used in eye drops and ointments in the treatment of minor eye infections. It typically exists as a hydrochloride salt. Dibromopropamidine has the following structure:

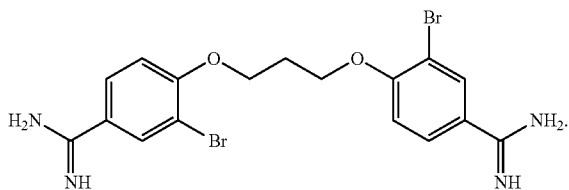 [SMILES: N=C(N)c1ccc(OCCCOc2ccc(C(=N)N)cc2Br)c(Br)c1]

Diminazene is another known amidine compound which is used as an anti-infective agent in animals. Commercial forms of the drug typically exist as an aceturate salt. The structure of diminazene aceturate is provided below:

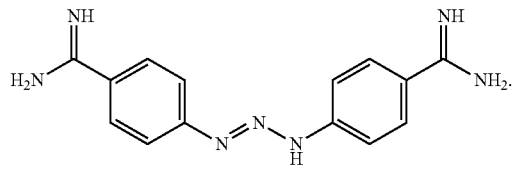 [SMILES: N=C(N)c1ccc(/N=N/Nc2ccc(C(=N)N)cc2)cc1]

The tetracycline family of compounds are known antibacterial agents and broad spectrum antibiotics. Their usefulness has been reduced by the onset of antibiotic resistance. However, they are still the treatment of choice in some indications.

Combinations of antibiotics are often used to treat bacterial infections. Combination therapies can provide increased efficacy and a reduction in the amount of each antibiotic thereby reducing the occurrence of undesirable side effects.

U.S. Pat. No. 7,947,741 describes the use and administration of pentamidine and related compounds as bacterial efflux pump inhibitors in combination with an antimicrobial agent to a subject infected with Gram-negative bacteria.

U.S. Pat. No. 7,994,225 describes efflux pump inhibitors to be co-administered with antimicrobial agents for the treatment of ophthalmic or otic infections. The agents may be co-administered directly to the site of infection (e.g. the eye or ear).

U.S. Pat. No. 5,204,113 describes pharmaceutical compositions suitable for administration by inhalation and containing pentamidine, or pharmaceutically acceptable salt thereof, in powder form and a method for the prevention or treatment of *Pneumacystics jorivecii* pneumonia which comprises administration by inhalation to a patient having or susceptible to that condition of a therapeutically effective quantity of pentamidine, or a pharmaceutically acceptable salt thereof, in powder form.

U.S. Pat. No. 6,677,133 describes a method of treating an infection caused by a drug resistant microbe in a subject, comprising administering a drug to which the microbe is resistant and an inhibitor of an AcrAB efflux pump to the subject such that the infection is treated.

GB2212394 discloses combinations of a sulpha antibacterials, particularly sulphadimidine and tetracycline antibiotics, particularly chlorotetracycline. The combinations disclosed are stated to have synergistic anti-bacterial effects, particularly against *Pasteurella* Spp. or *Boredetella* Spp.

Increased activity in vitro against multi-drug-resistant *P. aeruginosa* has been achieved by combinations of polymyxin A plus rifampin; ceftazidime or cefepime plus a quinolone; ceftazidime plus colistin; clarithromycin plus tobramycin; and azithromycin plus tobramycin, doxycycline, trimethoprim, or rifampin (J. J. Rahal in Antibiotic Combinations for Resistant Bacteria, CID, 43 (2006), suppl. 2, S95).

There is however, an ongoing need for new combination products to treat bacterial infections.

BRIEF SUMMARY OF THE DISCLOSURE

Combination Products

In a first aspect of the invention, there is provided a combination product comprising:
(i) an amidine selected from dibromopropamidine and diminazene, or a pharmaceutically acceptable salt or solvate thereof; and
(ii) a tetracycline anti-bacterial agent or a pharmaceutically acceptable salt, solvate or ester thereof;
for use in the treatment of an infection or disease caused by bacteria.

In another aspect of the invention, there is also provided a method of treating an infection or disease caused by bacteria in a subject, the method comprising administering to a subject a therapeutically effective amount of a combination product comprising;
(i) an amidine selected from dibromopropamidine and diminazene or a pharmaceutically acceptable salt or solvate thereof; and
(ii) a tetracycline anti-bacterial agent or a pharmaceutically acceptable salt, solvate or ester thereof.

In another aspect of the invention, there is provided a combination product comprising:
(i) an amidine selected from dibromopropamidine and diminazene, or a pharmaceutically acceptable salt or solvate thereof; and
(ii) a tetracycline anti-bacterial agent or a pharmaceutically acceptable salt, solvate or ester thereof;
for use in the treatment of an infection or disease caused by Gram-negative bacteria.

In another aspect of the invention, there is provided a method of treating a infection or disease caused by Gram-negative bacteria in a subject, the method comprising administering to a subject a therapeutically effective amount of a combination product comprising;
(i) an amidine selected from dibromopropamidine and diminazene or a pharmaceutically acceptable salt or solvate thereof; and
(ii) a tetracycline anti-bacterial agent or a pharmaceutically acceptable salt, solvate or ester thereof.

In another aspect of the invention, there is provided a combination product comprising:
(i) an amidine selected from dibromopropamidine and diminazene, or a pharmaceutically acceptable salt or solvate thereof; and
(ii) a tetracycline anti-bacterial agent or a pharmaceutically acceptable salt, solvate or ester thereof;
for use in the treatment of an infection or disease caused by Gram-positive bacteria.

In another aspect of the invention, there is provided a method of treating an infection or disease caused by Gram-positive bacteria in a subject, the method comprising administering to a subject a therapeutically effective amount of a combination product comprising;
(i) an amidine selected from dibromopropamidine and diminazene or a pharmaceutically acceptable salt or solvate thereof; and
(ii) a tetracycline anti-bacterial agent or a pharmaceutically acceptable salt, solvate or ester thereof.

In another aspect there, is provided a combination product comprising:
(i) an amidine selected from dibromopropamidine and diminazene, or a pharmaceutically acceptable salt or solvate thereof; and
(ii) a tetracycline anti-bacterial agent or a pharmaceutically acceptable salt, solvate or ester thereof;
for use in the treatment of:
(i) a dermatological condition of the skin, hair or nails, selected from infected acute and chronic dermatitis, skin and soft tissue infections, diabetic ulcers, dermatitis including atopic dermatitis, acne, impetigo, rosacea, chronic rhinosinusitis, decolonization of MRSA, pre-surgical decolonization and decolonization of dialysis patients; preferably wherein the combination product is for use in the treatment of diabetic ulcers; or
(ii) an ophthalmic condition or infection selected from eye diseases, ocular infections, acute and chronic uveitis, corneal ulceration, dry eye, conjunctivitis, acute conjunctivitis, chronic conjunctivitis, inclusion conjunctivitis, keratitis, blepharitis, canaliculitis, endophthalmitis, trachoma, and orbital or preseptal cellulitis.

Combination Products

In an embodiment, the combination product comprises dibromopropamidine, or a pharmaceutically acceptable salt or solvate thereof, and a tetracycline anti-bacterial agent or a pharmaceutically acceptable salt, solvate or ester thereof. The tetracycline may be any of the tetracycline compounds disclosed herein.

In another embodiment, the combination product comprises dibromopropamidine, or a pharmaceutically acceptable salt or solvate thereof, and a tetracycline anti-bacterial agent selected from the group consisting of tigecycline, doxycycline, minocycline, tetracycline, methacycline, meclocycline, demeclocycline, omadacycline, sarecycline, eravacycline, TP-271, TP-6076, chlortetracycline, oxytetracycline, rolitetracycline, lymecycline, pipacycline and sancycline, or a pharmaceutically acceptable salt, solvate or ester thereof.

In another embodiment, the combination product comprises dibromopropamidine or a pharmaceutically acceptable salt or solvate thereof, and a tetracycline selected from the group consisting of meclocycline, tigecycline, omadacycline, sarecycline, evracycline, TP-271, TP-6076, rolitetracycline, pipacycline and sancycline, or a pharmaceutically acceptable salt, solvate or ester thereof.

In an embodiment, the combination product comprises dibromopropamidine or a pharmaceutically acceptable salt or solvate thereof, and a tetracycline anti-bacterial agent selected from tigecycline, doxycycline, minocycline and tetracycline, or a pharmaceutically acceptable salt, solvate or ester thereof.

In an embodiment, the combination product comprises dibromopropamidine or a pharmaceutically acceptable salt or solvate thereof, and a tetracycline anti-bacterial agent selected from sarecycline, doxycycline, minocycline and tetracycline, or a pharmaceutically acceptable salt, solvate or ester thereof.

In an embodiment, there is provided a combination product comprising dibromopropamidine, or a pharmaceutically acceptable salt or solvate thereof, and doxycycline, or a pharmaceutically acceptable salt, solvate or ester thereof.

In an embodiment, there is provided a combination product comprising dibromopropamidine, or a pharmaceutically acceptable salt or solvate thereof, and minocycline, or a pharmaceutically acceptable salt, solvate or ester thereof. Suitably the minocycline is minocycline hydrochloride.

In an embodiment, there is provided a combination product comprising dibromopropamidine, or a pharmaceutically acceptable salt or solvate thereof, and tetracycline, or a pharmaceutically acceptable salt, solvate or ester thereof.

In an embodiment, there is provided a combination product comprising dibromopropamidine, or a pharmaceutically acceptable salt or solvate thereof, and tigecycline, or a pharmaceutically acceptable salt, solvate or ester thereof.

In an embodiment, the combination product comprises dibromopropamidine, or a pharmaceutically acceptable salt or solvate thereof, and a tetracycline anti-bacterial agent selected from doxycycline hyclate, minocycline hydrochloride, tetracycline hydrochloride and tigecycline hydrate.

In an embodiment, the combination product comprises diminazene or a pharmaceutically acceptable salt or solvate thereof and a tetracycline or a pharmaceutically acceptable salt, solvate or ester thereof, with the proviso that the tetracycline is not tigecycline or a pharmaceutically acceptable salt, solvate or ester thereof.

In various embodiments of the invention, the combination product comprises diminazene or a pharmaceutically acceptable salt or solvate thereof and a tetracycline anti-bacterial agent or a pharmaceutically acceptable salt, solvate or ester thereof. In some embodiments, the tetracycline is not tigecycline or a pharmaceutically acceptable salt, solvate or ester thereof. In other embodiments, the tetracycline is tigecycline or a pharmaceutically acceptable salt, solvate or ester thereof.

In an embodiment, the combination product comprises diminazene, or a pharmaceutically acceptable salt or solvate thereof, and a tetracycline selected from tigecycline, doxycycline, minocycline, tetracycline, methacycline, meclocycline, demeclocycline, omadacycline, sarecycline, eravacycline, TP-271, TP-6076, chlortetracycline, oxytetracycline, rolitetracycline, lymecycline, pipacycline and sancycline, or a pharmaceutically acceptable salt, solvate or ester thereof.

In an embodiment, the combination product comprises diminazene, or a pharmaceutically acceptable salt or solvate thereof, and a tetracycline selected from doxycycline, minocycline, tetracycline, methacycline, meclocycline, demeclocycline, omadacycline, sarecycline, eravacycline, TP-271, TP-6076, chlortetracycline, oxytetracycline, rolitetracycline, lymecycline and pipacycline, or a pharmaceutically acceptable salt, solvate or ester thereof.

In an embodiment, the combination product comprises diminazene or a pharmaceutically acceptable salt or solvate thereof, and a tetracycline anti-bacterial agent selected from sarecycline, doxycycline, minocycline and tetracycline, or a pharmaceutically acceptable salt, solvate or ester thereof.

In an embodiment, the combination product comprises diminazene, or a pharmaceutically acceptable salt or solvate thereof, and a tetracycline anti-bacterial agent selected from doxycycline, minocycline and tetracycline, or a pharmaceutically acceptable salt, solvate or ester thereof.

In another embodiment, the combination product comprises diminazene or a pharmaceutically acceptable salt or solvate thereof, and a tetracycline selected from the group consisting of meclocycline, tigecycline, omadacycline, sarecycline, evracycline, TP-271, TP-6076, rolitetracycline, pipacycline and sancycline, or a pharmaceutically acceptable salt, solvate or ester thereof.

The invention provides a combination product comprising diminazene, or a pharmaceutically acceptable salt or solvate thereof, and doxycycline, or a pharmaceutically acceptable salt, solvate or ester thereof.

In some embodiments when the combination product comprises diminazene, or a pharmaceutically acceptable salt or solvate thereof (e.g. diminazine aceturate), and doxycycline, or a pharmaceutically acceptable salt, solvate or ester thereof the composition does not comprise enrofloxacin.

In some embodiments when the combination product comprises diminazene, or a pharmaceutically acceptable salt or solvate thereof (e.g. diminazine aceturate), and doxycycline, or a pharmaceutically acceptable salt, solvate or ester thereof the composition does not comprise metronidazole.

In other embodiments when the combination product comprises diminazene, or a pharmaceutically acceptable salt or solvate thereof (e.g. diminazine aceturate), and doxycycline, or a pharmaceutically acceptable salt, solvate or ester thereof the composition does not comprise enrofloxacin or metronidazole.

The invention also provides a combination product comprising diminazene, or a pharmaceutically acceptable salt or solvate thereof, and minocycline, or a pharmaceutically acceptable salt, solvate or ester thereof. The invention also provides a combination product comprising diminazene, or a pharmaceutically acceptable salt or solvate thereof, and tetracycline, or a pharmaceutically acceptable salt, solvate or ester thereof.

In an embodiment, there is provided a combination product comprising diminazene, or a pharmaceutically acceptable salt or solvate thereof, and doxycycline or a pharmaceutically acceptable salt, solvate or ester thereof.

In an embodiment, there is provided a combination product comprising diminazene, or a pharmaceutically acceptable salt or solvate thereof, and minocycline or a pharmaceutically acceptable salt, solvate or ester thereof.

In an embodiment, there is provided a combination product comprising diminazene, or a pharmaceutically acceptable salt or solvate thereof, and tetracycline or a pharmaceutically acceptable salt, solvate or ester thereof.

In an embodiment, the combination product comprises diminazene, or a pharmaceutically acceptable salt or solvate thereof, and a tetracycline anti-bacterial agent selected from doxycycline hyclate, minocycline hydrochloride and tetracycline hydrochloride.

In a preferred embodiment, the combination product will comprise diminazene, or a pharmaceutically acceptable salt or solvate thereof, and a tetracycline anti-bacterial agent selected from doxycycline hyclate and minocycline hydrochloride.

In another aspect, there is provided a combination product comprising
(i) an amidine selected from dibromopropamidine and diminazene or a pharmaceutically acceptable salt or solvate thereof; and
(ii) a tetracycline anti-bacterial agent; wherein the tetracycline is selected from the group consisting of meclocycline, omadacycline, sarecycline, evracycline, TP-271, TP-6076, rolitetracycline, pipacycline and sancycline, or a pharmaceutically acceptable salt, solvate or ester thereof.

In certain embodiments, combination products defined herein do not comprise enrofloxacin and/or metronidazole.

In another aspect of the invention there is provided a combination product as defined herein for use as a medicament.

The combination products described above may be for use in the treatment of any of the bacterial infections or diseases described herein.

Also provided is the use of a combination product comprising an amidine and a tetracycline as defined herein, in the manufacture of a medicament for use in the treatment of an infection or disease caused by bacteria, for example an infection or disease caused by Gram-negative bacteria or an infection or disease caused by Gram-positive bacteria.

Tetracycline Anti-Bacterial Agent

The tetracycline anti-bacterial agent (also referred to herein as "tetracycline compound" or "tetracycline") present in the combination product may be selected from the group consisting of as tigecycline, doxycycline, minocycline, tetracycline, methacycline, meclocycline, demeclocycline, omadacycline, sarecycline, eravacycline, TP-271, TP-6076, chlortetracycline, oxytetracycline, rolitetracycline, lymecycline, pipacycline and sancycline, or a pharmaceutically acceptable salt, solvate or ester thereof.

The tetracycline compound may be selected from tigecycline, doxycycline, minocycline and tetracycline, or a pharmaceutically acceptable salt, solvate or ester thereof.

The tetracycline compound may be selected from sarecycline, doxycycline, minocycline and tetracycline, or a pharmaceutically acceptable salt, solvate or ester thereof. In a preferred embodiment, the tetracycline anti-bacterial agent is sarecycline or a pharmaceutically acceptable salt thereof.

The tetracycline of the combination product as disclosed herein may be a glycylcycline, for example tigecycline, or an aminomethylcycline, for example omadacycline. The tetracycline of the combination product may be any of the tetracycline compounds disclosed herein, for example a compound of the formula (I), (II), (III), (IV), (V) or (VI) as disclosed hereinafter, or a pharmaceutically acceptable salt, solvate or ester thereof.

The tetracycline of the combination product as disclosed herein may be selected from a glycylcycline, chlortetracycline, demeclocycline, doxycycline, lymecycline, methacycline, minocycline, oxytetracycline, tetracycline and tigecycline.

The tetracycline of the combination product may be selected from doxycycline, minocycline, tetracycline and tigecycline, or a pharmaceutically acceptable salt, solvate or ester thereof. For example, the tetracycline is selected from doxycycline hyclate, minocycline hydrochloride, tetracycline hydrochloride and tigecycline hydrate.

In another embodiment, the tetracycline of the combination product as disclosed herein may be selected from the group consisting of meclocycline, tigecycline, omadacycline, sarecycline, evracycline, TP-271, TP-6076, rolitetracycline, pipacycline and sancycline, or a pharmaceutically acceptable salt, solvate or ester thereof.

In an embodiment, tetracycline compound of the combination product as disclosed herein may be 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a C1-4-dedimethylaminotetracycline-4,6-hemiketal; 5a,6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a, 6 anhydrotetracycline; 4-methylamino-4-dedimethylamino tetracycline; 4-hydrazono-11α-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a C1-6,12 hemiketal tetracyclines; 11 a C1-6-methylene tetracyclines; 6, 13 diol tetracyclines; 6-benzylthiomethylene tetracyclines; 7, 11a-dichloro-6-fluoro-methyl-6-deoxy tetracyclines; 6-fluoro (a)-6-demethyl-6-deoxy tetracyclines; 6-fluoro (P)-6-demethyl-6-deoxy tetracyclines; 6-α acetoxy-6-demethyl tetracyclines; 6-β acetoxy-6-demethyl tetracyclines; 7, 13-epithiotetracyclines; oxytetracyclines; pyrazolotetracyclines; 11a halogens of tetracyclines; 12a formyl and other esters of tetracyclines; 5, 12a esters of tetracyclines; 10, 12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thiatetracyclines, including salts, solvates or esters thereof. In such embodiments, the combination product also comprises dibromopropamidine or diminazene or a pharmaceutically acceptable salt or solvate thereof.

In an embodiment, the tetracycline comprises a compound of the formula (I), or a pharmaceutically acceptable salt, solvate or ester thereof;

Formula (I)

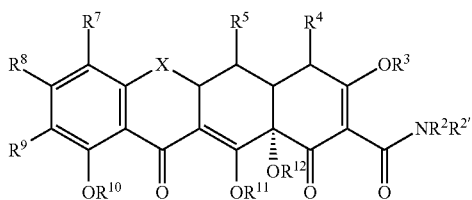

wherein:
X is $CHC(R^{13}Y'Y)$, $CR^{6'}R^6$, $C=CR^{6'}R^6$, S, $NR^6$, or O;
$R^2$ and $R^{2'}$ are each independently hydrogen, halogen, alkyl, haloalkyl, heteroalkyl, alkenyl, alkynyl, alkoxy, alkylthio, alkylsulfinyl, alkylsulfonyl, alkylamino, arylalkyl, aryl, cycloalkyl, heterocyclic, heteroaromatic, alkylheterocycyl, alkylheteroaromatic, —$CH_2R^{2''}$ or a prodrug moiety;
$R^{2''}$ is selected from an amino acid residue;
$R^3$, $R^{10}$, $R^{11}$ and $R^{12}$ are each independently hydrogen or a pro-drug moiety;
$R^4$ is $NR^4R^{4'}$, alkyl, alkenyl, alkynyl, aryl, hydroxyl, halogen, or hydrogen;
$R^{4'}$, and $R^{4''}$ are each independently hydrogen, halogen, alkyl, haloalkyl, heteroalkyl, alkenyl, alkynyl, alkoxy, alkylthio, alkylsulfinyl, alkylsulfonyl, alkylamino, arylalkyl, aryl, heterocyclic, heteroaromatic, alkylheterocycyl, alkylheteroaromatic or a prodrug moiety;
$R^5$ is hydroxyl, hydrogen, thiol, alkanoyl, aroyl, alkaroyl, aryl, heteroaryl, alkyl, haloalkyl, heteroalkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, haloalkyl, heteroalkyl, alkenyl, alkynyl, aryl, alkoxy, alkylthio, alkylsulfinyl, alkylsulfonyl, alkylamino, or an arylalkyl;

$R^7$ is independently hydrogen, halogen, hydroxyl, nitro, alkyl, haloalkyl, heteroalkyl, alkenyl, alkynyl, aryl, alkoxy, alkylthio, alkylsulfinyl, alkylsulfonyl, arylalkyl, alkylamino, amino, aminoalkyl, arylalkenyl, arylalkynyl, thionitroso, or $CR^{7a}R^{7b}NR^{7c}E$;
wherein E is alkyl, $NR^{7d}R^{7e}$, $OR^{7f}$ or $(CH_2)_{0-1}C(=W')WR^{7g}$; W is O, S, $NR^{7h}$ or $CR^{7i}R^{7j}$;
W' is O, S or $NR^{7h}$;
$R^{7a}$, $R^{7b}$, $R^{7c}$, $R^{7d}$, $R^{7e}$, $R^{7f}$, $R^{7g}$, $R^{7h}$, $R^{7i}$ and $R^{7j}$ are each independently hydrogen, allyl, alkyl, alkenyl, alkynyl, hydroxyl, alkoxy, alkylthio, alkylsulfinyl, alkylsulfonyl, amino, alkylamino, aminoalkyl, acyl, aryl, arylalkyl, alkylcarbonyloxy, alkylcarbonyloxyalkyl or arylcarbonyloxy, or $R^{7c}$ and $R^{7d}$ or $R^{7c}$ and $R^{7f}$ are linked to form a ring;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^9$ is independently hydrogen, hydroxyl, nitro, alkyl, haloalkyl, heteroalkyl, alkenyl, alkynyl, aryl, alkoxy, alkylthio, alkylsulfinyl, alkylsulfonyl, arylalkyl, alkylamino, amino, arylalkenyl, arylalkynyl, thionitroso, —$CJ^7J^8NJ^5J^6$, —$(CH_2)_mNR^{9c}C(=Z')ZR^{9a}$;
wherein $J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;
$J^7$ and $J^8$ are each alkyl, halogen, or hydrogen;
wherein m is an integer selected from 0, 1, 2 and 3;
Z is —$CR^{9d}R^{9e}$—, —S—, —$NR^{9b}$— or —O—;
Z' is O, S, or $NR^{9f}$;
$R^{9a}$, $R^{9b}$, $R^{9c}$ and $R^{9f}$ are each independently hydrogen, acyl, alkyl, amino, alkenyl, alkynyl, alkoxy, alkylthio, alkylsulfinyl, alkylsulfonyl, alkylamino, arylalkyl, aryl, heterocyclic, heteroaryl or a prodrug moiety;
$R^{9d}$, and $R^{9e}$ are each independently hydrogen, acyl, alkyl, amino, alkenyl, alkynyl, alkoxy, alkylthio, alkylsulfinyl, alkylsulfonyl, alkylamino, arylalkyl, aryl, heterocyclic, heteroaryl or a prodrug moiety; or may be joined together to form a cyclic or heterocyclic ring;
$R^{13}$ is hydrogen, hydroxyl, alkyl, alkenyl, alkynyl, alkoxy, alkylthio, alkylsulfinyl, alkylsulfonyl, alkylamino, or an arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters, and prodrugs thereof.

In a preferred embodiment, the tetracycline is a compound as described in U.S. RE40183 E1. Preferably, the compound is tigecycline or a pharmaceutically acceptable salt, solvate, ester, or prodrug thereof.

Glycylcyclines

Glycylcyclines include bulky N,N-dimethylglycylamido at position 9 of minocycline. This results in the compound being less susceptible to tetracycline resistance mediated by acquired efflux pumps and/or ribosomal protection.

In an embodiment, the tetracycline of the combination product as disclosed herein is a glycylcycline compound according to formula II below, or a pharmaceutically acceptable salt, solvate or ester thereof:

Formula II

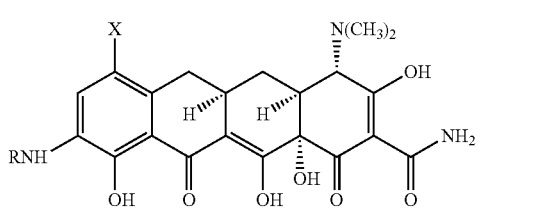

wherein;

X is selected from amino; $NR^1R^2$, or halogen selected from bromine, chlorine, fluorine or iodine;

$R^1$ is selected from hydrogen, methyl, ethyl, n-propyl, 1-methylethyl, n-butyl and 1-methylpropyl;

$R^2$ is selected from methyl, ethyl, n-propyl, 1-methylethyl, n-butyl, 1-methylpropyl, 2-methylpropyl, and 1,1-dimethylethyl, provided that when X is $NR^1R^2$ and $R^1$ is hydrogen, $R^2$ is methyl, ethyl, n-propyl, 1-methylethyl, n-butyl, 1-methylpropyl, 2-methylpropyl or 1,1-dimethylethyl;

and when $R^1$ is methyl or ethyl; $R^2$ is methyl, ethyl, n-propyl, 1-methylethyl, n-butyl, 1-methylpropyl or 2-methylpropyl;

and when $R^1$ is n-propyl, $R^2$ is n-propyl, 1-methylethyl, n-butyl, 1-methylpropyl or 2-methylpropyl;

and when $R^1$ is 1-methylethyl, $R^2$ is n-butyl, 1-methylpropyl or 2-methylpropyl;

and when $R^1$ is n-butyl, $R^2$ is n-butyl, 1-methylpropyl or 2-methylpropyl;

and when $R^1$ is 1-methylpropyl, $R^2$ is 2-methylpropyl;

R is selected from $R^4(CH_2)_nCO—$ or $R^{4'}(CH_2)_nSO_2—$; and n is 0-4;

and when R is $R^4(CH_2)_nCO—$ and n is 0, $R^4$ is selected from amino; monosubstituted amino selected from straight or branched $(C_1-C_6)$alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazolyl, 1-pyrrolyl, 1-(1,2,3-triazolyl) or 4-(1,2,4-triazolyl); a substituted $(C_3-C_6)$cycloalkyl group with substitution selected from cyano, amino or $(C_1-C_3)$ acyl; a substituted $(C_6-C_{10})$aryl group with substitution selected from halo, $(C_1-C_4)$alkoxy, trihalo $(C_1-C_3)$-alkyl, nitro, amino, cyano, $(C_1-C_4)$alkoxycarbonyl $(C_1-C_3)$alkylamino or carboxy; α-amino-$(C_1-C_4)$alkyl selected from aminomethyl, α-aminoethyl, α-aminopropyl or α-aminobutyl; carboxy $(C_2-C_4)$-alkylamino selected from aminoacetic acid, α-aminobutyric acid or α-aminopropionic acid and the optical isomers thereof; $(C_7-C_9)$aralkylamino; $(C_1-C_4)$alkoxycarbonylamino substituted $(C_1-C_4)$ alkyl group; α-hydroxy$(C_1-C_3)$alkyl selected from hydroxymethyl, α-hydroxyethyl or α-hydroxy-1-methylethyl or α-hydroxypropyl; α-mercapto $(C_1-C_3)$alkyl selected from mercaptomethyl, α-mercaptoethyl, α-mercapto-1-methylethyl or α-mercaptopropyl; halo-$(C_1-C_3)$alkyl group; a heterocycle selected from the group consisting of a five membered aromatic or saturated ring with one N, O, S or Se heteroatom optionally having a benzo or pyrido ring fused thereto, a five membered aromatic ring with two N, O, S, or Se heteroatoms optionally having a benzo or pyrido ring fused thereto, a six membered aromatic ring with one to three N, O, S or Se heteroatoms, or a six membered saturated ring with one or two N, O, S or Se heteroatoms and an adjacent appended O heteroatom; acyl or haloacyl group selected from acetyl, propionyl, chloroacetyl, trifluoroacetyl; $(C_3-C_6)$cycloalcyl-carbonyl, $(C_6-C_{10})$aroyl selected from benzoyl or naphthoyl; halo substituted $(C_6-C_{10})$aroyl; $(C_1-C_4)$ alkylbenzoyl, or (heterocycle)-carbonyl, the heterocycle as defined hereinabove; $(C_1-C_4)$alkoxycarbonyl selected from methoxycarbonyl, ethoxycarbonyl, straight or branched propoxylcarbonyl, straight or branched butoxycarbonyl or allyloxycarbonyl; a substituted vinyl group with substitution selected from halogen, halo$(C_1-C_3)$alkyl, or a substituted $(C_6-C_{10})$aryl group with substitution selected from halo, $(C_1-C_4)$-alkoxy, trihalo$(C_1-C_3)$alkyl, nitro, amino, cyano, $(C_1-C_4)$alkoxycarbonyl, $(C_1-C_3)$alkylamino or carboxy; $(C_1-C_4)$alkoxy group; $C_6$-aryloxy selected from phenoxy or substituted phenoxy with substitution selected from halo, $(C_1-C_4)$ alkyl, nitro, cyano, thiol, amino, carboxy, di$(C_1-C_3)$ alkylamino; $(C_7-C_{10})$aralkyloxy; vinyloxy or a substituted vinyloxy group with substitution selected from $(C_1-C_4)$ alkyl, cyano, carboxy, or $(C_6-C_{10})$aryl selected from phenyl, α-naphthyl, or β-naphthyl; $R^aR^b$ amino$(C_1-C_4)$alkoxy group, wherein $R^aR^b$ is a straight or branched $(C_1-C_4)$alkyl selected from methyl, ethyl, n-propyl, 1-methylethyl, n-butyl, 1-methylpropyl, or 2-methylpropyl or $R^aR^b$ is $(CH_2)_m$, m is 2-6, or $(CH_2)_2W(CH_2)_2—(CH_2)_2W(CH_2)_2—$ wherein W is selected from $—N(C_1-C_3)$alkyl, O, S, —NH, —NOB and B is selected from hydrogen or $(C_1-C_3)$alkyl; or $R^aR^b$ aminoxy group, wherein $R^aR^b$ is straight or branched $(C_1-C_4)$alkyl selected from methyl, ethyl, n-propyl, 1-methylethyl, n-butyl, 1-methylpropyl, 2-methylpropyl, or 1,1-dimethylethyl or $R^aR^b$ is $(CH_2)_m$, m is 2-6, or $—(CH_2)_2W(CH_2)_2—$ wherein W is selected from $—N(C_1-C_3)$alkyl, O, S, —NH, —NOB and B is selected from hydrogen or $(C_1-C_3)$alkyl;

and when R is $R^4(CH_2)_nCO—$ and n is 1-4, $R^4$ is selected from amino; a substituted $(C_3-C_6)$cycloalkyl group with substitution selected from cyano, amino or $(C_1-C_3)$acyl; a substituted $(C_6-C_{10})$-aryl group with substitution selected from halo, $(C_1-C_4)$-alkoxy, trihalo$(C_1-C_3)$alkyl, nitro, amino, cyano, $(C_1-C_4)$alkoxycarbonyl, $(C_1-C_3)$alkylamino or carboxy; acyloxy or haloacyloxy group selected from acetyl, propionyl, chloroacetyl, trichlorocetyl, $(C_3-C_6)$cycloalkylcarbonyl, $(C_6-C_{10})$aroyl selected from benzoyl or naphthoyl, halo substituted $(C_6-C_{10})$aroyl, $(C_1-C_4)$alkylbenzoyl, or (heterocycle)-carbonyl, the heterocycle as defined hereinabove; $(C_1-C_4)$alkoxy; $C_6$-aryloxy selected from phenoxy or substituted phenoxy with substitution selected from halo, $(C_1-C_4)$-alkyl, nitro, cyano, thiol, amino, carboxy, di$(C_1-C_3)$-alkylamino; $(C_7-C_{10})$aralkyloxy; $(C_1-C_3)$alkylthio group selected from methylthio, ethylthio, propylthio or allylthio; $C_6$-arylthio group selected from phenylthio or substituted phenylthio with substitution selected from halo, $(C_1-C_4)$alkyl, nitro, cyano, thiol, amino, carboxy, di$(C_1-C_3)$ alkylamino; $C_6$-arylsulfonyl group selected from phenylsulfonyl or substituted phenylsulfonyl with substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy; $(C_7-C_8)$aralkylthio group; a heterocycle as defined hereinabove; hydroxy; mercapto; mono- or distraight or branched chain $(C_1-C_6)$-alkylamino with the alkyl selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-methylbutyl, 2,2-dimethylbutyl, 2-methylpentyl, 1,2-dimethylbutyl, 1,3-dimethylbutyl or 1-methyl-1-ethylpropyl; $(C_2-C_5)$azacycloalkyl group; a carboxy$(C_2-C_4)$ alkylamino group with the carboxy alkyl selected from aminoacetic acid, α-aminopropionic acid, α-aminobutyric acid and the optical isomers thereof; α-hydroxy$(C_1-C_3)$alkyl selected from hydroxymethyl, α-hydroethyl or α-hydroxy-1-methylethyl or α-hydropropyl; halo($C_1$-$C_3$)alkyl group; acyl or haloacyl selected from acetyl, propionyl, chloroacetyl, trifluoroacetyl; ($C_3$-$C_6$)cycloalkylcarbonyl; ($C_6$-$C_{10}$) aroyl selected from benzoyl or naphthoyl; halo substituted ($C_6$-$C_{10}$)aroyl; ($C_1$-$C_4$)alkylbenzoyl, or (heterocycle)carbonyl, wherein the heterocycle is as defined hereinabove; ($C_1$-$C_4$)alkoxycarbonylamino, a group selected from tert-butoxycarbonylamino, allyloxycarbonylamino, methoxycarbonylamino, ethoxycarbonylamino or propoxycarbonylamino; ($C_1$-$C_4$)alkoxycarbonyl group selected from methoxycarbonyl, ethoxycarbonyl, straight or branched propoxycarbonyl, allyloxycarbonyl or straight or branched butoxycarbonyl; $R_aR^b$-amino($C_1$-$C_4$)alkoxy group wherein $R^aR^b$ is straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH)_m(CH_2)_m$ m is 2-6 or —$(CH_2)_2W(CH_2)_2$— wherein W is selected from —N($C_1$-$C_3$)-alkyl, O, S, —NH, —NOB, and B is selected from hydrogen or ($C_1$-$C_3$)alkyl; or $R^aR^b$ aminoxy group, wherein $R^aR^b$ is straight or branched ($C_1$-$C_4$)-alkyl selected from methyl, ethyl, n-propyl, 1-methylethyl, n-butyl, 1-methylpropyl, 2-methylpropyl or $R^aR^b$ is $(CH_2)_m$, m is 2-6, or —$(CH_2)_2W(CH_2)_2$— wherein W is selected from —N($C_1$-$C_3$)-alkyl, O, S, —NH, —NOB and B is selected from hydrogen or ($C_1$-$C_3$)alkyl, and when R is $R^{4'}(CH_2)SO_2$—R=$R^{4'}(CH_2)_nSO_2$— and n=0, $R^{4'}$ is selected from amino; monosubstituted amino selected from straight or branched ($C_1$-$C_6$)alkylamino, cyclopropylamino, cyclobutylamino, benzylamino or phenylamino; disubstituted amino selected from dimethylamino, diethylamino, ethyl(1-methylethyl)amino, monomethylbenzylamino, piperidinyl, morpholinyl, 1-imidazoyl, 1-pyrrolyl, 1-(1,2,3-triazolyl) or 4-(1,2,4-triazolyl); a substituted ($C_3$-$C_6$)cycloalkyl group with substitution selected from cyano, amino or ($C_1$-$C_3$)acyl; halo($C_1$-$C_3$)alkyl group; a heterocycle as defined hereinabove;

$R^aR^b$ amino ($C_1$-$C_4$)alkoxy group, wherein $R^aR^b$ is a straight or branched ($C_1$-$C_4$)-alkyl selected from methyl, ethyl, n-propyl, 1-methyl-ethyl, n-butyl, 1-methylpropyl, or 2-methylpropyl or $R^aR^b$ is $(CH_2)_m$, m=2-6, or —$(CH_2)_2W$—$(CH_2)_2$— wherein W is selected from —N($C_1$-$C_3$) alkyl, O, S, —NH, —NOB and B is selected from hydrogen or ($C_1$-$C_3$)-alkyl; or $R^aR^b$ aminoxy group, wherein $R^aR^b$ is a straight or branched ($C_1$-$C_4$)alkyl selected from methyl, ethyl, n-propyl, 1-methylethyl, n-butyl, 1-methyl-propyl, or 2-methyl-propyl or $R^aR^b$ is $(CH_2)_m$, m=2-6, or —$(CH_2)_2W(CH_2)_2$— wherein W is selected from —N($C_1$-$C_3$)alkyl, O, S, —NY—NH, —NOB and B is selected from hydrogen or ($C_1$-$C_3$) alkyl; and when R is $R^4(CH_2)_nSO_2$— and n is 1-4, $R^{4'}$ is selected from ($C_1$-$C_4$)carboxyalkyl; a substituted ($C_3$-$C_6$)cycloalkyl group with substitution selected from cyano, amino or ($C_1$-$C_3$)-acyl; ($C_1$-$C_4$)alkoxy; $C_6$-aryloxy selected from phenoxy or substituted phenoxy with substitution selected from halo, ($C_1$-$C_3$)alkyl, nitro, cyano, thiol, amino, carboxy, di($C_1$-$C_3$) alkylamino; ($C_7$-$C_{10}$)aralkyoxy; $R^aR^b$ amino ($C_1$-$C_4$) alkoxy, wherein $R^aR^b$ is a straight or branched ($C_1$-$C_4$)-alkyl selected from methyl, ethyl, n-propyl, 1-methylethyl, n-butyl, 1-methylpropyl, or 2-methylpropyl or $R^aR^b$ is $(CH_2)_m$, m is 2-6, or —$(CH_2)_2W(CH_2)_2$— wherein W is selected from —N($C_1$-$C_3$)alkyl, O, S, —NY—NH or —NOB and B is selected from hydrogen or ($C_1$-$C_3$)alkyl; or $R^aR^b$ aminoxy group, wherein $R^aR^b$ is straight or branched ($C_1$-$C_4$)alkyl selected from methyl, ethyl, n-propyl, 1-methylethyl, n-butyl, 1-methylpropyl, or 2-methylpropyl or $R^aR^b$ is $(CH_2)_m$, m is 2-6, or —$(CH_2)_2W(CH_2)_2$— wherein W is selected from —N($C_1$-$C_3$)alkyl, O, S, —NH, —NOB and B is selected from hydrogen or ($C_1$-$C_3$)alkyl; ($C_1$-$C_3$) alkylthio selected from methylthio, ethylthio or n-propylthio; $C_6$-arylthio selected from phenylthio or substituted phenylthio with substitution selected from halo, ($C_1$-$C_3$)alkyl, nitro, cyano, thiol, amino, carboxy, di($C_1$-$C_3$) alkylamino; ($C_7$-$C_8$) aralkylthio; a heterocycle as defined hereinabove; hydroxy; mercapto; mono- or di-straight or branched ($C_1$-$C_6$)alkyl-amino group the alkyl selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl or 1-methyl-1-ethylpropyl; halo ($C_1$-$C_3$) alkyl; acyl or haloacyl selected from acetyl, propionyl, chloro-acetyl, trifluoroacetyl; ($C_3$-$C_6$) cycloalkylcarbonyl; ($C_6$-$C_{10}$) aroyl selected from benzoyl or naphthoyl; halo substituted ($C_6$-$C_{10}$)aroyl, ($C_1$-$C_4$) alkylbenzoyl, or (heterocycle) carbonyl, the heterocycle as defined hereinabove; ($C_1$-$C_4$)alkoxycarbonyl selected from methoxycarbonyl, ethoxycarbonyl, straight or branched propoxycarbonyl, allyloxycarbonyl or straight or branched butoxycarbonyl; $R^5$ is selected from hydrogen; straight or branched ($C_1$-$C_3$) alkyl selected from methyl, ethyl n-propyl or 1-methylethyl; ($C_6$-$C_{10}$)aryl selected from phenyl, α-naphthyl or β-naphthyl; ($C_7$-$C_9$) aralkyl group; a heterocycle as defined hereinabove; or —$(CH_2)_nCOOR^7$ where n is 0-4 and $R^7$ is selected from hydrogen; straight or branched ($C_1$-$C_3$)alkyl group selected from methyl, ethyl, n-propyl or 1-methylethyl; or ($C_6$-$C_{10}$)aryl group selected from phenyl, α-naphthyl or β-naphthyl;

$R^6$ is selected from hydrogen, straight or branched ($C_1$-$C_3$) alkyl group selected form methyl, ethyl, n-propyl or 1-methylethyl; ($C_6$-$C_{10}$)aryl group selected from phenyl, α-naphthyl or β-naphthyl; ($C_7$-$C_9$)-aralkyl group; a heterocycle as defined hereinabove; or —$(CH_2)_n(COOR^{7'})'$ where n is 0-4 and $R^{7'}$ is selected from hydrogen; straight or branched ($C_1$-$C_3$)alkyl selected from methyl, ethyl, n-propyl or 1-methylethyl; or ($C_6$-$C_{10}$)aryl selected from phenyl, α-naphthyl or β-naphthyl; with the proviso that $R^5$ and $R^6$ cannot both be hydrogen;

or $R^5$ and $R^6$ taken together are —$(CH_2)_2W(CH_2)_2$—, wherein W is selected from $(CH_2)_q$ and q is 0-1, —NH, —N($C_1$-$C_3$)-alkyl, —N($C_1$-$C_4$) alkoxy, oxygen, sulfur or substituted congeners selected from (L or D) proline, ethyl (L or D) prolinate, morpholine, pyrrolidine or piperidine;

and the pharmacologically acceptable organic and inorganic salts or metal complexes thereof.

In an embodiment, the combination product comprises a compound according to formula II; wherein X is selected from amino, $NR^1R^2$, or halogen, for example bromine, chlorine, fluorine or iodine, and when X is $NR^1R^2$, $R^1$ is methyl or ethyl and $R^2$ is methyl or ethyl; R is $R^4(CH_2)_nCO$—; n is 1-4; and $R^4$ is monosubstituted or disubstituted amino selected from straight or branched ($C_1$-$C_6$)alkylamino, with the alkyl selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethybutyl or 1-methyl-1-ethylpropyl and pharmacologically acceptable organic and inorganic salts or metal complexes.

In an embodiment, the combination product will comprise a compound of formula II, wherein X is $N(CH_3)_2$ and R is $R^4(CH_2)_nCO$— wherein n is 1-4 and $R^4$ is monosubstituted or disubstituted amino selected from straight or branched ($C_1$-$C_6$)alkylamino, with the alkyl selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl or 1-methyl-1-ethylpropyl and pharmacologically acceptable organic and inorganic salts or metal complexes.

In a preferred embodiment, the tetracycline is a glycylcycline compound as described in U.S. RE40183 E1. In an embodiment, the combination product will comprise a compound of formula II wherein X is $N(CH_3)_2$ and R is $R^4(CH_2)_nCO$— where n is 1 and $R^4$ is monosubstituted or disubstituted amino selected from straight or branched ($C_1$-$C_6$)alkylamino, with the alkyl selected from methyl, ethyl, n-propyl, 1-methylethyl, n-butyl, 1-methylpropyl, 2-methylpropyl, 1,1-dimethylethyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 2-methylpentyl, 1,2-dimethylbutyl, 1,3-dimethylbutyl or 1-methyl-1-ethylpropyl and pharmacologically acceptable organic and inorganic salts or metal complexes. Preferably, the compound is tigecycline or a pharmaceutically acceptable salt, solvate, ester, or prodrug thereof.

Aminomethyl Cyclines

The tetracycline of the combination product as disclosed herein may be an aminiomethylcycline. Aminomethylcyclines are further derivatives of tetracycline compounds. Aminomethylcyclines include further substitution at the "9" or "7" position of a minocycline derivative. An example of an aminomethylcycline is omadacycline.

In an embodiment, the combination product comprises a compound of formula III;

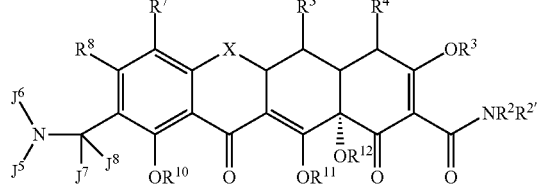

Formula III wherein $J^5$ and $J^6$ are each independently hydrogen, alkyl, alkenyl, alkynyl, aryl, sulfonyl, acyl, alkoxycarbonyl, alkaminocarbonyl, alkaminothiocarbonyl, substituted thiocarbonyl, substituted carbonyl, alkoxythiocarbonyl, or linked to form a ring;
$J^7$ and $J^8$ are each independently alkyl, halogen, or hydrogen;
X is $CHC(R^{13}Y'Y)$, $CR^6R^{6'}$, $C=CR^6R^{6'}$, S, $NR^6$, or O;
$R^2$, $R^{2'}$, $R^{4'}$, and $R^4$ are each independently hydrogen, alkyl, alkenyl, alkynyl, alkoxy, alkylthio, alkylsulfinyl, alkylsulfonyl, alkylamino, arylalkyl, aryl, heterocyclic, heteroaryl or a prodrug moiety;
$R^4$ is $NR^{4'}R^{4''}$, alkyl, alkenyl, alkynyl, aryl, hydroxyl, halogen, or hydrogen;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaryl, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ and $R^8$ are each independently hydrogen, hydroxyl, halogen, amino, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts thereof.

The tetracycline compound may be an aminomethylcycline disclosed within WO2003075857A2. Preferably, $R^2$, $R^{2'}$, $R^3$, $R^5$, $R^8$, $R^{10}$, $J^7$ and $J^8$ are hydrogen, R is $NR^{4'}R^{4''}$, $R^{4'}$ and $R^{4''}$ are each methyl, X is $CR^6R^{6'}$, $R^6$ and $R^{6'}$ are each hydrogen and $R^7$ is $N(CH^3)^2$) In another embodiment, $J^5$ may be substituted or unsubstituted alkyl, sulfonyl, heteroaryl or substituted carbonyl and $J^6$ may be hydrogen, alternatively $J^5$ and $J^6$ may be linked to form a ring. A preferred compound according to Formula III is omadacyline.

In an embodiment, the tetracycline of the combination product as disclosed herein is a compound according to Formula IV below;

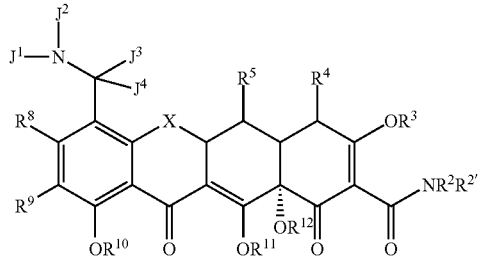

Formula IV wherein,
$J^1$ and $J^2$ are each independently hydrogen, aryl, sulfonyl, acyl, or linked to form a ring, provided that at least one of $J^1$ or $J^2$ is not hydrogen;
$J^3$ and $J^4$ are each alkyl, halogen, or hydrogen;
X is $CHC(R^{13}Y'Y)$, $CR^6R^{6'}$, $C=CR^6R^{6'}$, S, $NR^6$, or O;
$R^2$, $R^{2'}$, $R^{4'}$, and $R^4$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety; $R^4$ is $NR^4R^4$, alkyl, alkenyl, alkynyl, aryl, hydroxyl, halogen, or hydrogen;
$R^3$, $R^{10}$, $R^{11}$ and $R^{12}$ are each independently hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^9$ is hydrogen, nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or —$(CH_2)_{0-3}NR^{9c}C(=Z')ZR^{9a}$; Z is $CR^{9d}R^{9e}$, S, $NR^{9b}$ or O;
Z' is O, S, or $NR^{9f}$;
$R^{9a}$, $R^{9b}$, $R^{9c}$, $R^{9d}$, and $R^{9e}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, or pharmaceutically acceptable salts, esters, or prodrugs thereof.

In an embodiment, the tetracycline of the combination product as disclosed herein is a substituted tetracycline compound disclosed in WO2008079339. In this embodiment, the compound may be a compound of Formula (V) below:

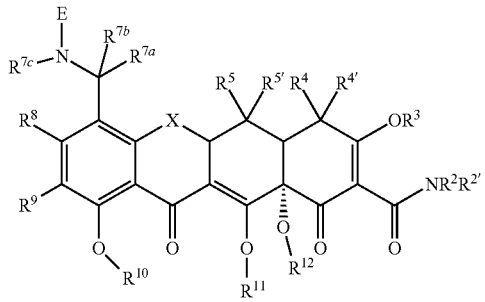

Formula (V)

wherein;
X is CHC(R$^{13}$Y$^3$Y), CR$^6$R$^6$, C=CR$^6$R$^6$, S, NR$^6$, or O;
E is NR$^{7d}$R$^{7e}$, OR$^{7f}$ or (CH$_2$)$_{0-1}$C(=W')WR$^{7g}$;
W is O, S, NR$^{7h}$ or CR$^{7i}$R$^{7i}$;
W' is O, S or NR$^{7k}$;
R$^2$, R$^{2'}$, R$^{4'}$, R$^{4a}$ and R$^{4b}$ are each independently hydrogen, alkyl, alkenyl, alkynyl, alkoxy, alkylthio, alkylsulfinyl, alkylsulfonyl, alkylamino, arylalkyl, aryl, heterocyclic, hetero aromatic or a prodrug moiety; R$^3$, R$^{10}$, R$^{11}$ and R$^{12}$ are each hydrogen or a pro-drug moiety;
R$^4$ is NR$^{4a}$R$^{4b}$, alkyl, alkenyl, alkynyl, hydroxyl, halogen, or hydrogen;
R$^5$ and R$^{5'}$ are each hydroxyl, hydrogen, thiol, alkanoyl, aroyl, alkaroyl, aryl, heteroaryl, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^{7a}$, R$^{7b}$, R$^{7c}$, R$^{7d}$, R$^{7e}$, R$^{7f}$, R$^{7g}$, R$^{7h}$, R$^{7i}$, R$^{7j}$ and R$^{7k}$ are each independently hydrogen, allyl, alkyl, alkenyl, alkynyl, hydroxyl, alkoxy, alkylthio, alkylsulfinyl, alkylsulfonyl, amino, alkylamino, aminoalkyl, acyl, aryl, arylalkyl, alkylcarbonyloxy, alkylcarbonyloxyalkyl or arylcarbonyloxy, or R$^{7c}$ and R$^{7d}$ or R$^{7c}$ and R$^{7f}$ are linked to form a ring;
R$^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
R$^9$ is hydrogen, nitro, alkyl, alkenyl, alkynyl, aryl, alkoxy, alkylthio, alkylsulfinyl, alkylsulfonyl, arylalkyl, amino, aminoalkyl, amido, arylalkenyl, arylalkynyl, thionitroso, or —(CH$_2$)$_{0-3}$(NR$^{9c}$)$_{0-1}$C(=Z')ZR$^{9a}$; Z is CR$^{9d}$R$^{9e}$, S, NR$^{9b}$ or O; Z' is O, S, or NR$^{9f}$; R$^{9a}$, R$^{9b}$, R$^{9c}$, R$^{9d}$, R$^{9e}$ and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, hetero aromatic or a prodrug moiety;

R$^{13}$ is hydrogen, hydroxy, alkyl, alkenyl, alkynyl, alkoxy, alkylthio, alkylsulfinyl, alkylsulfonyl, alkylamino, or an arylalkyl; and Y' and Y are each independently hydrogen, halogen, hydroxyl, cyano, sulfhydryl, amino, amido, alkyl, alkenyl, alkynyl, alkoxy, alkylthio, alkylsulfinyl, alkylsulfonyl, alkylamino, or an arylalkyl, or pharmaceutically acceptable salts thereof.

In an embodiment, the tetracycline may be a compound disclosed in WO2008079339. In a preferred embodiment, the tetracycline is a compound according to Formula (V) wherein E is OR$^{7f}$ and R$^{7f}$ is alkyl, with the remaining substituents defined according to Formula (V). Preferably, in such an embodiment, the compound may be sarecycline:

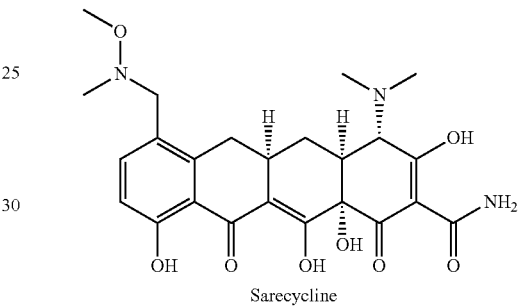

Sarecycline or a pharmaceutically acceptable salty, solvate or ester thereof.

The tetracycline compound may also be represented by Formula (VI);

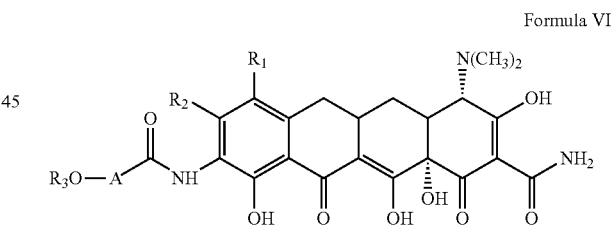

Formula VI wherein:
A is a moiety:

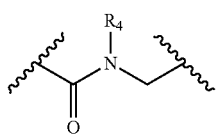

R$_1$ is selected from hydrogen, —OH, amino, —NR$_7$R$_8$, halogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aryloxy, heterocyclyl and phenyl, and alkynyl of 2 to 12 carbon atoms optionally substituted with 1 to 3 substituents independently selected from the group halogen, amino, cyano, alkyl, hydroxyl, and alkoxy;

$R_2$ is selected from halogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, and alkynyl of 2 to 12 carbon atoms optionally substituted with 1 to 3 substituents independently selected from the group halogen, amino, cyano, alkyl, hydroxyl, and alkoxy;

$R_3$ is selected from the moiety:

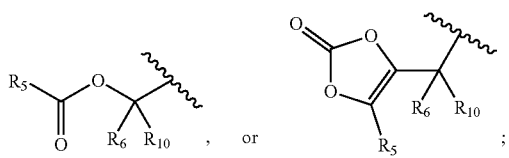

$R_4$ is selected from hydrogen, alkyl of 1 to 12 carbon atoms, optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkenyl of 2 to 12 carbon atoms optionally substituted with 1 to 3 substituents independently selected from the group phenyl, heteroaryl, halogen, amino, cyano, alkyl, hydroxyl, alkoxy, aryl, alkynyl and N-(alkyl of 1 to 12 carbon atoms)-aryl, wherein said aryl and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, alkynyl of 2 to 12 carbon atoms optionally substituted with 1 to 3 substituents independently selected from the group halogen, amino, cyano, alkyl, hydroxyl, and alkoxy, aryl of 6, 10 or 14 carbon atoms said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, N-(alkyl of 1 to 12 carbon atoms)-aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl of 7 to 13 carbon atoms optionally substituted, $SR^3$, heteroaryl optionally substituted and heteroarylcarbonyl optionally substituted;

$R_5$ is selected from alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl of 6, or 14 carbon atoms, aryloxy and N-(alkyl of 1 to 12 carbon atoms)-aryl, wherein said aryl, aryloxy and aryl of N-(alkyl of 1 to 12 carbon atoms)-aryl, may be optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, aralkyl of 7 to 16 carbon atoms optionally substituted, aroyl, —$CH_2$(CO)O$CH_2$aryl, said aryl optionally substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryloxy and phenyl, alkenyl of 2 to 12 carbon atoms optionally substituted, heteroaryl optionally substituted, aryl of 6, 10 or 14 carbon atoms optionally substituted, alkynyl of 2 to 12 carbon atoms optionally substituted, cycloalkyl 3 to 6 ring atoms, aryl-CH=CH—, cycloalkyl-alkyl; and adamantly;

$R_6$ is selected from hydrogen, alkyl of 1 to 12 carbon atoms optionally substituted with 1 to 3 substituents independently selected from the group halogen, amino, cyano, cycloalkyl of 3 to 6 carbon atoms, alkyl of 1 to 12 carbon atoms, phenyl, hydroxyl, alkoxy of 1 to 12 carbon atoms, N-alkyl of 1 to 12 carbon atoms, N-cycloalkyl of 3 to 6 carbon atoms, heterocyclyl of 3 to 8 ring atoms, aryl, aryloxy and N-(alkyl of 1 to 12 carbon atoms)-aryl, wherein said aryl, aryloxy and aryl of N-(alkyl of 1 to 12 carbon atoms)-aryl may optionally be substituted with 1 to 3 substituents independently selected from halogen, nitro, cyano, alkenyl, hydroxyl, alkyl, haloalkyl, alkoxy, amino, alkylamino, dialkylamino, carboxyl, alkoxycarbonyl, aryl-C(O)—, $CH_3$—C(O)—NH—, aralkyl, aryloxy, heterocyclyl and phenyl, and cycloalkyl of 3 to 6 carbon atoms;

$R_7$ and $R_8$ are each independently H or $R_7$ and $R_8$ when optionally taken together with the nitrogen atom to which each is attached form a 3 to 8 membered heterocyclyl ring; $R_{10}$ is H or alkyl of 1 to 12 carbon atoms;
or a pharmaceutically acceptable salt, solvate or ester thereof.

In a preferred embodiment the tetracycline of the combination product as disclosed herein is selected from one of the compounds listed in the table below, or a pharmaceutically acceptable salt, solvate or ester thereof:

| Compound | Structure |
| --- | --- |
| chlortetracycline | 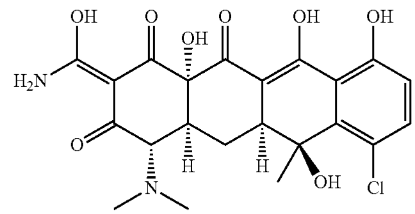 [SMILES: CN(C)[C@@H]1C(=O)/C(=C(\N)O)C(=O)[C@@]2(O)C(=O)C3=C(O)c4c(O)ccc(Cl)c4[C@@](C)(O)[C@H]3C[C@@H]12] |
| demeclocycline | 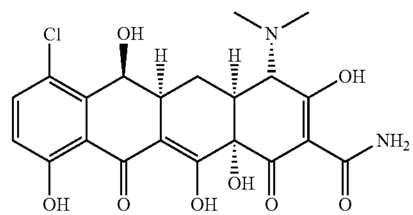 |
| doxycycline | 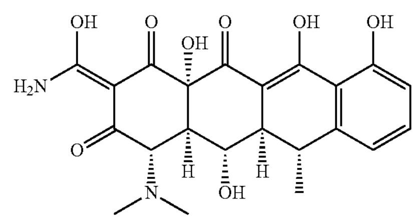 [SMILES: C[C@H]1c2cccc(O)c2C(O)=C2C(=O)[C@]3(O)C(=O)/C(=C(/N)O)C(=O)[C@@H](N(C)C)[C@@H]3[C@@H](O)[C@@H]21] |
| meclocycline | 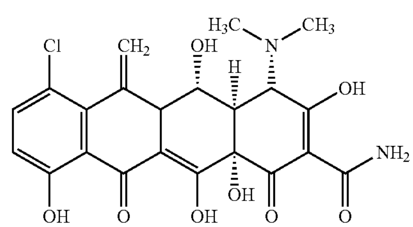 |
| methacycline | 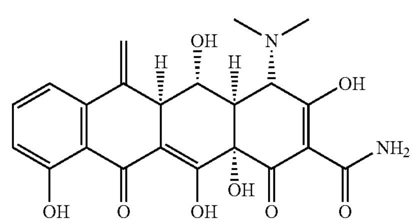 |
| minocycline | 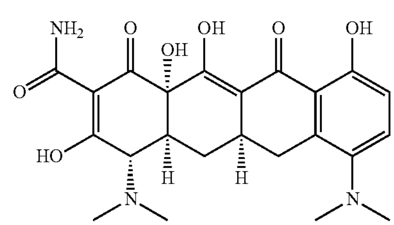 [SMILES: CN(C)c1ccc(O)c2c1C[C@H]1C[C@H]3[C@H](N(C)C)C(O)=C(C(N)=O)C(=O)[C@@]3(O)C(O)=C1C2=O] |

| Compound | Structure |
|---|---|
| tetracycline | 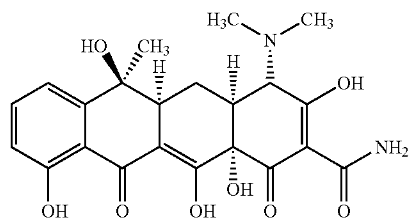 |
| tigecycline | 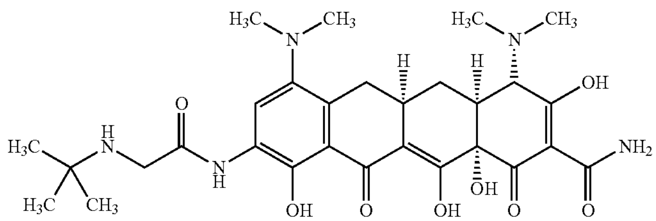 |
| omadacycline | 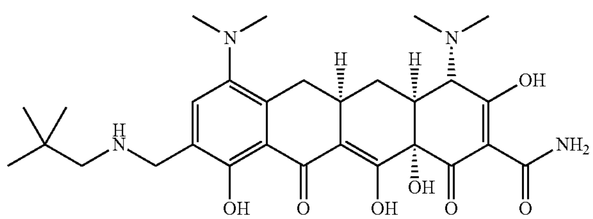 |
| sarecycline | 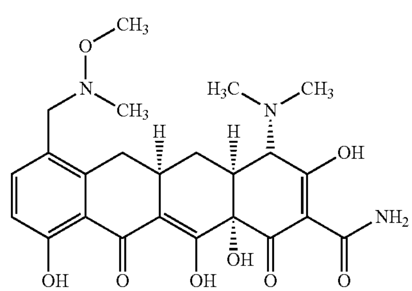 |
| eravacycline | 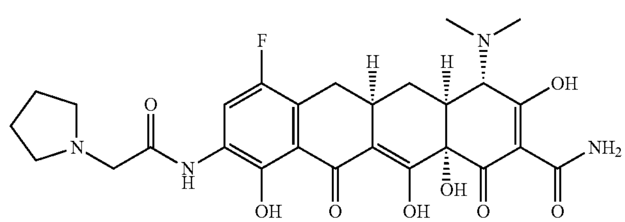 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12] |
| TP-271 | 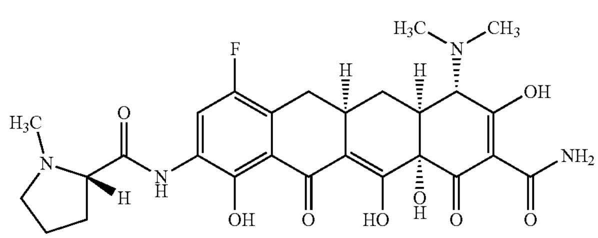 [SMILES: CN(C)[C@@H]1C(O)=C(C(N)=O)C(=O)[C@@]2(O)C(O)=C3C(=O)c4c(O)c(NC(=O)[C@@H]5CCCN5C)cc(F)c4C[C@H]3C[C@@H]12] |

| Compound | Structure |
|---|---|
| oxytetracycline | 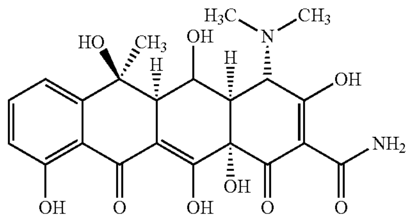 |
| rolitetracycline | 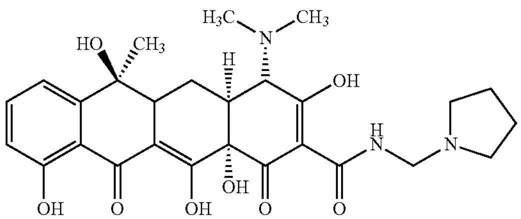 |
| lymecycline | 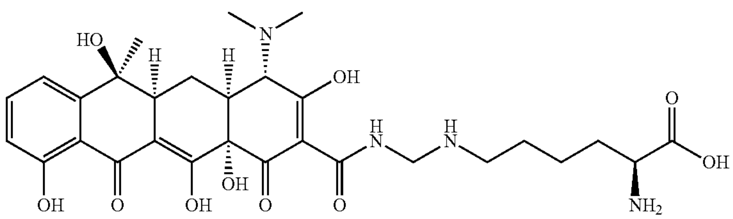 [SMILES: CN(C)[C@@H]1C(O)=C(C(=O)NCNCCCC[C@H](N)C(=O)O)C(=O)[C@@]2(O)C(O)=C3C(=O)c4c(O)cccc4[C@@](C)(O)[C@H]3C[C@@H]12] |
| pipacycline | 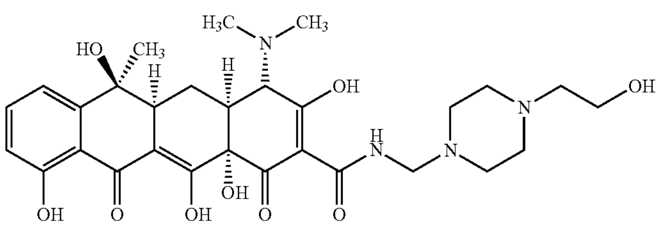 |
| sancycline | 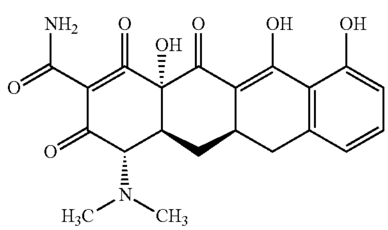 |

In some embodiments, the tetracycline of the combination product as disclosed herein is not chlortetracycline, or a pharmaceutically acceptable salt, solvate or ester thereof.

It will be understood that the tetracyclines as defined herein may also exist in one or more tautomeric forms. For example, as illustrated by two possible tautomeric forms of chlortetracycline.

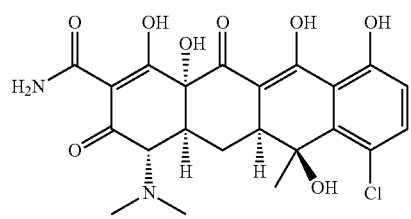

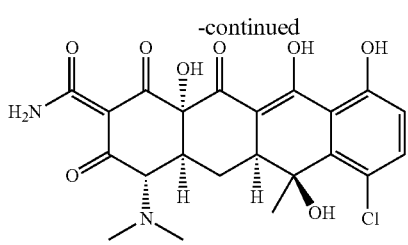

In the above example, it will also be understood that the ketone and hydroxyl groups on the middle two rings may also tautomerise. The present invention encompasses all tautomeric forms of tetracyclines which exhibit antibacterial activity.

Treatment of Infections/Diseases

The combination products described herein are expected to provide a beneficial treatment of bacterial infections and diseases, preferably a synergistic treatment effect compared to the use of the amidine alone or the tetracycline alone In an aspect of the invention there is a provided combination product as defined herein for use as a medicament. The combination product may be for use in the treatment of a bacterial infection or a disease caused by a bacterial infection. The combination product may be for use in the treatment of an infection or disease caused by Gram-negative bacteria as defined herein. The combination product may also be for use in the treatment of an infection or disease caused by Gram-positive bacteria as defined herein.

In an embodiment, the infection or disease to be treated is caused by bacteria selected from any one or more of *Staphylococcus aureus* and *S. epidermidis*; various species of the genus *Streptococcus*, including *S. pyogenes* and *S. pneumoniae*; *Escherichia coli*; various species of *Klebsiella*, including *K. pneumoniae*; and various species of *Enterobacter*, *Enterococcus* and Acenitobacter.

Gram-Negative Bacteria

In an embodiment, the combination product of the invention may be for use in the treatment of an infection or disease caused by Gram-negative bacteria. The invention thus provides a method of treating a subject having an infection or disease caused by Gram-negative bacteria. The method of treatment may comprise administering to a subject a therapeutically effective amount of a combination product described herein.

In an embodiment, the Gram-negative bacteria which cause the disease or infection are selected from *Pseudomonas aeruginosa, Pseudomonas fluorescens, Pseudomonas acidovorans, Pseudomonas alcaligenes, Pseudomonas putida, Stenotrophomonas maltophilia, Achromobacter xylosoxidans, Burkholderia cepacia, Aeromonas hydrophilia, Escherichia coli, Citrobacter freundii, Salmonella typhimurium, Salmonella typhi, Salmonella paratyphi Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi Pasteurella multocida, Pasteurella haemolytica, Branhamella catarrhalis, Helicobacter pylori Campylobacter fetus, Campylobacter jejuni Campylobacter coli Borrelia burgdorferi Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii*, and *Bacteroides splanchnicus*. The combination products disclosed herein may be used in the treatment of an infection or disease caused by any of the above bacteria. Thus, there is provided a method of treating diseases or infections caused by any of the above bacteria. The method of treatment may comprise administering to a subject a therapeutically effective amount of a combination product described herein.

The infection or disease to be treated may be caused by the bacteria *Pseudomonas aeruginosa*. Subjects with weakened immune systems due to another illness or condition are most susceptible to *Pseudomonas aeruginosa* infections. Conditions which may increase the risk of infection include burn wounds, chemotherapy cancer patients, patients with cystic fibrosis, HIV or AIDS patients, or a patient undergoing an invasive procedure such as surgery. Subjects with a foreign body implant such as a mechanical ventilator or catheter are also at risk of infection, for example infection by *Pseudomonas aeruginosa* infections.

In an embodiment, the infection or disease to be treated may be caused by the bacteria *Escherichia coli*.

The combination products of the invention may be used in the treatment of an infection or disease caused by the bacteria *Pseudomonas aeruginosa*.

In an embodiment, the combination product of the invention may be used in the treatment of diseases or infections of the lungs caused by the bacteria *Pseudomonas aeruginosa*. Thus, there is provided a method of treating diseases or infections of the lungs caused by the bacteria *Pseudomonas aeruginosa*. The method of treatment may comprise administering to a subject a therapeutically effective amount of a combination product described herein.

The infection or disease may be caused by the bacteria *Escherichia coli*. In an embodiment, the combination product of the invention may be used in the treatment of diseases or infections caused by the bacteria *Escherichia coli*. Thus, there is provided a method of treating diseases or infections caused by *Escherichia coli*. The method of treatment may comprise administering to a subject a therapeutically effective amount of a combination product described herein.

As illustrated in the Examples certain combination products are particularly effective against Gram-negative bacteria, for example *Pseudomonas aeruginosa* and/or *E. coli*.

In an embodiment, there is provided a combination product comprising dibromopropamidine or a pharmaceutically acceptable salt or solvate thereof, and a tetracycline anti-bacterial agent selected from tigecycline, doxycycline, minocycline and tetracycline, or a pharmaceutically acceptable salt, solvate or ester thereof, for use in the treatment of an infection or a disease caused by bacteria selected from *Pseudomonas aeruginosa* and/or *E. coli*.

A further embodiment, provides a combination product comprising dibromopropamidine or a pharmaceutically acceptable salt or solvate thereof, and a tetracycline anti-bacterial agent selected from doxycycline and minocycline, or a pharmaceutically acceptable salt, solvate or ester thereof, for use in the treatment of an infection or a disease caused by *Pseudomonas aeruginosa*.

In another embodiment, there is provided a combination product comprising diminazene or a pharmaceutically acceptable salt or solvate thereof, and a tetracycline anti-bacterial agent selected from tigecycline, doxycycline, minocycline and tetracycline, or a pharmaceutically acceptable salt, solvate or ester thereof, for use in the treatment of an infection or a disease caused by bacteria selected from *Pseudomonas aeruginosa* and/or *E. coli*.

A further embodiment provides a combination product comprising diminazene or a pharmaceutically acceptable salt or solvate thereof, and a tetracycline anti-bacterial agent selected from doxycycline, minocycline and tetracycline (preferably selected from doxycycline and minocycline), or a pharmaceutically acceptable salt, solvate or ester thereof, for use in the treatment of an infection or a disease caused by *Pseudomonas aeruginosa*.

In another embodiment, there is provided a combination product comprising diminazene or a pharmaceutically acceptable salt or solvate thereof, and a tetracycline anti-bacterial agent selected from tigecycline, doxycycline and minocycline (preferably tigecycline), or a pharmaceutically acceptable salt, solvate or ester thereof, for use in the treatment of an infection or a disease caused by *E. coli*.

Gram-Positive Bacteria

In an embodiment, the combination product of the invention may be for use in the treatment of an infection or disease caused by Gram-positive bacteria. The invention thus provides a method of treating a subject having an infection or disease caused by Gram-positive bacteria. The method of treatment may comprise administering to a subject a therapeutically effective amount of a combination product described herein.

In an embodiment, the infection or disease may be caused by Gram-positive bacteria selected from *Actinomyces, Arthrobacter, Bifidobacterium, Corynebacterium, Frankia, Micrococcus, Micromonospora, Mycobacterium, Nocardia, Propionibacterium, Streptomyces, Bacillus, Listeria, Staphylococcus, Enterococcus, Lactobacillus, Lactococcus, Leuconostoc, Pediococcus, Streptococcus, Acetobacterium, Clostridium, Eubacterium, Heliobacterium, Heliospirillum, Megasphaera, Pectinatus, Selenomonas, Zymophilus, Sporomusa, Mycoplasma, Spiroplasma, Ureaplasma* and *Erysipelothrix*.

In an embodiment the infection or disease may be caused by Gram-positive bacteria selected from *Staphylococcus* (including, for example, *S. aureus* spp., *S. epidermidis* spp., *S. warneri* spp. and *S. haemolyticus* spp., *Streptococcus* (including, for example, *S. viridans* spp., *S. pneumoniae* spp., *S. agalactiae* spp., and *S. pyogenes* spp., *Bacillus* (including, for example, *B. anthracis* spp. and *B. subtilis*, spp., *Clostridium* (including, for example, *C. difficile* spp., *Propionibacterium* (including, for example, *P. acnes* spp., *Enterococcus* (including, for example, *E. faecium* spp., *E. faecalis* spp., Vancomycin-resistant *E. faecium* spp., and Vancomycin-resistant *E. faecalis* spp., and *Mycobacterium* (including, for example, *M. smegmatis* spp. and *M. tuberculosis* spp.).

In an embodiment, the infection or disease may be caused by Gram-positive bacteria selected from *Bacillus anthracis, Bacillus cereus, Clostridium botulinum, Clostridium tetani, Clostridium difficile, Clostridium perfringens, Corynebacterium diptheriae, Listeria monocytogenes, Staphylococcus aureus*, including methicillin-resistant *Staphylococcus aureus, Enterococcus, Streptococcus agalactiae, Streptococcus pyogenes* and *Streptococcus pneumoniae*.

In an embodiment, the infection or disease may be caused by the bacterium *Staphylococcus aureus*.

In an embodiment, the infection or disease may be caused by the bacterium *Streptococcus pyogenes*.

Antibiotic Resistance

The combination product according to the invention has particular application in the treatment of infections or diseases caused by bacteria which are resistant to one or more antibiotics. Gram-negative bacteria are resistant to multiple drugs and are increasingly resistant to most available antibiotics. The combination product of the present invention has been found to be effective against antibiotic resistant Gram-negative bacteria.

In an embodiment, the infection or disease is caused by an organism resistant to one or more antibiotics.

The Gram-negative bacteria and Gram-positive bacteria described herein may be resistant to one or more antibiotic drugs. In an embodiment, the combination product may be for use in the treatment of Gram-negative bacteria which are resistant to one or more antibiotics. Thus, there is provided a method of treating an infection or disease caused by an antibiotic resistant Gram-negative or Gram-positive bacteria, the method comprising administering to the subject a therapeutically effective amount of a combination product as described herein. Suitably the Gram-negative or Gram-positive bacteria are resistant to an antibiotic other than dibromopropamidine and diminazene.

Historically, tetracyclines are considered first generation if they are obtained by biosynthesis such as: tetracycline, chlortetracycline, oxytetracycline, demeclocycline. Second generation tetracyclines are derivatives of semi-synthesis such as: doxycycline, lymecycline, meclocycline, methacycline, minocycline and rolitetracycline. Third generation tetracyclines are obtained from total synthesis such as tigecycline. In an embodiment, the infection or disease is caused by bacteria resistant to tetracycline or any member of first, second or third generation of tetracycline antibiotics.

In an embodiment, the infection or disease is caused by bacteria which is not an antibiotic resistant strain. In another embodiment, the infection or disease is caused by bacteria which is an antibiotic resistant strain In another embodiment, the infection or disease is caused by bacteria resistant to methicillin.

In another embodiment, the infection or disease is caused by bacteria resistant to vancomycin.

In another embodiment, the infection or disease is caused by bacteria resistant to a quinolone or fluoroquinolone.

In another embodiment, the infection or disease is caused by bacteria resistant to tigecycline or any other tetracycline derivative. In a particular embodiment, the infection is caused by an organism resistant to tigecycline.

In an embodiment, the infection or disease is caused by bacteria which is resistant to compounds other than the amidines and tetracyclines disclosed herein. In another embodiment, the infection or disease is caused by bacteria which is resistant to an amidine, for example dibromopropamidine and/or diminazene. In another embodiment, the infection or disease is caused by bacteria which is resistant to a tetracycline antibacterial agent, for example any of the tetracycline compounds disclosed herein.

Infections/Diseases

As stated herein, the combination products may be used in the treatment of bacterial infections or diseases. Such combination products have particular application in the treatment of dermatological and ophthalmic conditions. The combination products also have particular application in the treatment of cystic fibrosis. In some embodiments, the combination products disclosed herein are for use in the treatment of bacterial biofilm infections.

The combination products described herein may be used in the treatment of infections or diseases caused by Gram-negative bacteria. The combination products described herein may also be used in the treatment of infections or diseases caused by Gram-positive bacteria.

In an embodiment, the infection or disease to be treated is selected from wound infections, including burn wound infections and diabetic wound infections; dermatological infections, skin and soft tissue infections; bacterial biofilm infections; diabetic ulcers; dermatitis including atopic dermatitis; lung infections, including pneumonia, cystic fibrosis and COPD; urinary tract infections; GI tract infections; acute leukaemia; organ transplants; intravenous-drug addiction; otitis; endophthalmitis; endocarditis; meningitis; septicaemia; septic shock; leukopenia, neutropenia, gastrointestinal infections, bone infections, joint infections, skin infections, ophthalmic conditions and infections, eye infections and combinations thereof.

The combination products have particular application in the treatment of ophthalmic conditions and infections. The infection or disease may be an ophthalmic condition or infection.

The combination products have particular application in the treatment of cystic fibrosis and bacterial biofilm infections.

The combination products have particular application in the treatment of diabetic ulcers. The infection or disease may be a diabetic ulcer.

The infection or disease may be an infection of the airway, lungs, urinary tract, a burn infection, a wound infection, a dermatological infection, an ophthalmic infection or a blood infection.

The infection or disease may be caused by Gram-negative or Gram-positive bacteria as described herein. The infection or disease may be selected from but not limited to an infection of the airway, urinary tract, a burn infection, a wound infection, blood infections, chronic wound infections, diabetic wound infections, diabetic ulcer, venous leg ulcers, dermatological infections, ophthalmic surgical wounds, inflammatory disorders, corneal ulceration, bronchiectasis, chronic pulmonary obstructive disease, skin and eye diseases, periodontitis, skin tissue wounds, dry eye, chronic conjunctivitis, inclusion conjunctivitis, keratitis, blepharitis, canaliculitis, endophthalmitis, trachoma, acute and chronic uveitis, and orbital or preseptal cellulitis, acute and chronic bronchitis, sinusitis, and respiratory infections, including the common cold, Wegener's granulomatosis; acute and chronic cystitis and urethritis; infected acute and chronic dermatitis; acute and chronic conjunctivitis, acute and chronic serositis, uremic pericarditis; acute and chronic cholecystis, cystic fibrosis, acute and chronic vaginitis, skin wound, food-borne illnesses, water-borne illnesses, skin infections, GI infections, urinary tract infections, genitourinary infections, respiratory tract infections, sinus infections, middle ear infections, systemic infections, intra-abdominal infections, pyelonephritis, pneumonia, bacterial vaginosis, streptococcal sore throat, chronic bacterial prostatitis, gynaecological and pelvic infections, sexually transmitted bacterial diseases, ocular and otic infections, cholera, influenza, bronchitis, acne, rosacea, chronic rhinosinusitis, decolonization of MRSA, pre-surgical decolonization and decolonization of dialysis patients, impetigo, sexually transmitted disease including syphilis and gonorrhoea, Legionnaires' disease, Lyme disease, hospital acquired infections, leptospirosis, anthrax and infections caused by the agents responsible for lymphogranuloma venereum, inclusion conjunctivitis, or psittacosis, burn wound infections; skin and soft tissue infections; bacterial biofilm infections; diabetic ulcers; dermatitis including atopic dermatitis; lung infections, including pneumonia, cystic fibrosis and COPD; urinary tract infections; GI tract infections; endocarditis; meningitis; septicaemia; gastrointestinal infections, bone infections, joint infections, skin infections, eye infections and combinations thereof.

The infection or disease may be a dermatological condition of the skin, hair or nails. The dermatological condition may be caused by any of the bacteria disclosed herein. The dermatological condition may be selected from but is not limited to infected acute and chronic dermatitis, skin and soft tissue infections, diabetic ulcers, dermatitis including atopic dermatitis, acne, impetigo, rosacea, chronic rhinosinusitis, decolonization of MRSA, pre-surgical decolonization and decolonization of dialysis patients. Preferably the infection or disease will be a diabetic ulcer.

In an embodiment, the dermatological condition may be caused by Gram-negative bacteria. In an embodiment, the dermatological condition may be caused by Gram-positive bacteria. The combination products disclosed herein may be used in the treatment of dermatological condition. The invention thus provides a method of treating a dermatological condition by administering to a subject a therapeutically effective amount of a combination product described herein. In the treatment of dermatological conditions, the combination product may be administered topically.

The infection or disease may be an ophthalmic condition or infection. The ophthalmic condition or infection may be caused by any of the bacteria disclosed herein. The ophthalmic condition or infection may be one selected from eye diseases, ocular infections, acute and chronic uveitis, corneal ulceration, dry eye, conjunctivitis, acute conjunctivitis, chronic conjunctivitis, inclusion conjunctivitis, keratitis, blepharitis, canaliculitis, endophthalmitis, trachoma, and orbital or preseptal cellulitis.

In an embodiment, there is provided a combination product comprising dibromopropamidine or a pharmaceutically acceptable salt or solvate thereof, and a tetracycline anti-bacterial agent selected from tigecycline, doxycycline, minocycline and tetracycline, or a pharmaceutically acceptable salt, solvate or ester thereof, for use in the treatment of an ophthalmic condition or infection.

A further embodiment provides a combination product comprising dibromopropamidine or a pharmaceutically acceptable salt or solvate thereof, and a tetracycline anti-bacterial agent selected from doxycycline and minocycline, or a pharmaceutically acceptable salt, solvate or ester thereof, for use in the treatment of an ophthalmic condition or infection.

In another embodiment, there is provided a combination product comprising diminazene or a pharmaceutically acceptable salt or solvate thereof, and a tetracycline anti-bacterial agent selected from tigecycline, doxycycline, minocycline and tetracycline, or a pharmaceutically acceptable salt, solvate or ester thereof, for use in the treatment of an ophthalmic condition or infection.

A further embodiment provides a combination product comprising diminazene or a pharmaceutically acceptable salt or solvate thereof, and a tetracycline anti-bacterial agent selected from doxycycline, minocycline and tetracycline (preferably selected from doxycycline and minocycline), or a pharmaceutically acceptable salt, solvate or ester thereof, for use in the treatment of an ophthalmic condition or infection.

In an embodiment, the ophthalmic condition or infection may be caused by Gram-negative bacteria. In an embodiment, the ophthalmic condition or infection may be caused by Gram-positive bacteria. The combination products disclosed herein may be used in the treatment of an ophthalmic condition or infection. The invention thus provides a method of treating an ophthalmic condition or infection by administering to a subject a therapeutically effective amount of a combination product described herein. In the treatment of ophthalmic conditions or infections, the combination product may be administered topically.

The infection or disease may be of the lungs or airway and may be chronic inflammatory lung disease, pulmonary fibrosis, pulmonary vasculitis, pulmonary sarcoidosis, inflammation and/or infection associated with lung transplantation, acute lung rejection, pulmonary artery hypertension, bronchitis, sinusitis, asthma, cystic fibrosis, bacterial infection (e.g., by *Pseudomonas aeruginosa*, anthrax, *Mycobacterium*) fungal infection (e.g., by *Aspergillus*, *Pneumocystis*

*carnii*), chronic obstructive pulmonary disease (COPD), bronchiolitis obliterans syndrome (BOS), primary ciliary dyskinesia (PCD), idiopathic pulmonary fibrosis (IPF), alveolar protienosis, eosinophilic pneumonia, eosinophilic bronchitis, acute respiratory distress syndrome (ARDS), inflammation and/or infection associated with mechanical ventilation, ventilator-associated pneumonia, asbestos-related airway disorder or disease, dust-related airway disorder or disease, silicosis, chemical agent-related airway disease or disorder and any combination thereof.

In an embodiment, the infection or disease is selected from wound infections, including burn wound infections and diabetic wound infections; skin and soft tissue infections; bacterial biofilm infections; diabetic ulcers; a dermatological condition of the skin, hair or nails; dermatitis including atopic dermatitis; lung infections, including pneumonia, cystic fibrosis and COPD; urinary tract infections; GI tract infections; otitis; endophthalmitis; endocarditis; meningitis; septicaemia; gastrointestinal infections, bone infections, joint infections, skin infections, ophthalmic conditions including eye infections and combinations thereof.

The infection or disease may be a chronic wound infection caused by any one or more of the bacteria selected from *Pseudomonas aeruginosa, Staphylococcus aureus* and *S. epidermidis*; various species of the genus *Streptococcus*, including *S. pyogenes* and *S. pneumoniae; Escherichia coli*; various species of *Klebsiella*, including *K. pneumoniae*; various species of *Enterobacter, Enterococcus* and Acenitobacter.

In an aspect of the invention there is provided a method of treating, preventing or eliminating bacterial colonization by Gram-negative or Gram-positive bacteria in a subject, the method comprising administering to the subject a therapeutically effective amount of a combination product as described herein. There is also provided a combination product as defined herein for use in preventing or eliminating bacterial colonization by Gram-negative or Gram-positive bacteria in a subject. For example the combination product may be for use in preventing or eliminating bacterial colonization by Gram-negative or Gram-positive bacteria in a subject with acute or chronic dermatitis (including atopic dermatitis) or diabetic ulcers.

Diabetic Ulcers

The combination product described herein may be for use in the treatment or prevention of infected diabetic ulcers, for example a diabetic foot ulcer. The diabetic foot ulcer may be infected by any Gram-negative or Gram-positive bacteria described herein. The diabetic foot ulcer may be infected by any of *Staphylococcus aureus* and *S. epidermidis*; various species of the genus *Streptococcus*, including *S. pyogenes* and *S. pneumoniae; Escherichia coli*; various species of *Klebsiella*, including *K. pneumoniae*; various species of *Enterobacter, Enterococcus* and Acenitobacter.

The combination product disclosed herein may be used in the treatment of diabetic ulcers. The diabetic ulcers may be caused by any of the Gram-negative and Gram-positive bacteria listed herein. The invention thus provides a method of treating diabetic ulcers by administering to a subject a therapeutically effective amount of a combination product described herein. In an embodiment, the combination product may be topically administered to a diabetic ulcer.

In preferred embodiment, there is provided a combination product comprising dibromopropamidine, or a pharmaceutically acceptable salt or solvate thereof, and minocycline, or a pharmaceutically acceptable salt, solvate or ester thereof, for use in the treatment of diabetic ulcers.

Methods of Treatment

The invention also provides a method of treating an infection or disease caused by any of the bacteria listed herein, the method comprising administering to a subject in need thereof a therapeutically effective amount of a combination product described herein comprising an amidine selected from dibromopropamidine and diminazene or a pharmaceutically acceptable salt or solvate thereof in combination with a tetracycline anti-bacterial agent or a pharmaceutically acceptable salt, solvate or ester thereof. The tetracycline anti-bacterial agent may be any tetracycline as defined herein.

The invention also provides a method of treating an infection or disease caused by *Pseudomonas aeruginosa*, the method comprising administering to a subject in need thereof a therapeutically effective amount of an amidine selected from dibromopropamidine and diminazene in combination with a tetracycline anti-bacterial agent. The tetracycline anti-bacterial agent may be any tetracycline as defined herein.

Biofilms

As discussed hereinbefore, it is increasingly recognized that infecting pathogens can enter a biofilm state in which complicates antibiotic treatment. Biofilms are believed to be relevant in various types of infections including chronic lung infections, wound infections and infections related to indwelling catheters. Cells in a biofilm state often show a reduced growth rate or enter a persistent state, which is sometimes associated with increased tolerance towards antibiotics. The biofilm structure itself may also limit access of antibiotics to the target cells thereby also contributing to a lower efficacy of antibiotic treatment.

The invention has particular applications in the treatment of bacterial biofilm infections. When bacteria succeed in forming biofilms in a subject, e.g. human hosts, infections can become untreatable. Chronic biofilm-based infections are extremely resistant to antibiotics and many other conventional antimicrobial agents, and have the capacity to evade host defences. The inventors have found that the combination products of the present invention can be used in the treatment of bacterial biofilm infections. Specifically, the combination products can be used to treat bacterial biofilm infections which are caused by Gram-negative bacteria or Gram-positive bacteria. The combination products can be used to treat bacterial biofilm infections which are caused by the bacterium *Pseudomonas aeruginosa*.

Infections where biofilms may be implicated include, for example bacterial vaginosis, urinary tract infections, diabetic ulcers, diabetic wounds, catheter infections, middle-ear infections, formation of dental plaque, gingivitis, and more lethal processes such as endocarditis, infections in cystic fibrosis, and infections of permanent indwelling devices such as joint prostheses and heart valves. Biofilms are also known to coat contact lenses, causing eye infections.

The combination products disclosed herein may be used in the treatment of bacterial biofilm infections caused by any of the bacteria described herein. In particular, the combination products may be used in the treatment of bacterial biofilm infections caused by *Pseudomonas aeruginosa*. The invention thus provides a method of treating bacterial biofilm infections by administering to a subject a therapeutically effective amount of a combination product described herein. In an embodiment, the combination product may be topically administered to a bacterial biofilm infection.

Administration

The combination products described herein may be formulated into a pharmaceutical composition.

In some embodiments, the combination product of the invention may be formulated for topical administration. The topical administration can be to the skin, e.g., to an area of intact or non-intact skin. Non-intact skin can include, but is not limited to, skin lesions, vesicles, chronic ulcers, cysts, blisters, bullae, open sores such as decubitus ulcers (bed sores) and other pressure sores, cellulitis sores, erysipelas lesions, wounds, burn wounds, carbuncles, cutaneous ulcers, e.g., cutaneous ulcers associated with diabetic foot infections, or other conditions where the skin is damaged, broken, cracked, breached and/or otherwise compromised.

In an embodiment, pharmaceutical composition of the invention can be formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, gel, foam, ointment or spray applied to the skin; (4) intravaginally or intrarectally, for example, as a pessary, cream, foam, or suppository; or (5) aerosol, for example, as an aqueous or non-aqueous aerosol, liposomal preparation or solid particles containing the compound.

In an embodiment, the combination product of the present invention may be administered orally, parenterally, by inhalation, or topically.

The combination product of the present invention may be topically administered. Alternatively, the combination product may be administered by inhalation. In certain embodiments, the combination product may be administered orally. In certain embodiments, the combination product may be administered parenterally.

The combination product may be nebulised for delivery to the lungs by inhalation. Nebulisation of antibiotics offers the possibility of delivering high lung tissue concentrations of antibiotics in normal and infected lungs by nasal inhalation.

In certain embodiments, the combination product may be administered by different routes, for example one compound may be administered orally and the other by inhalation.

Formulations

The invention provides a pharmaceutical formulation comprising an amidine selected from dibromopropamidine and diminazene, or a pharmaceutically acceptable salt or solvate thereof; a tetracycline or a pharmaceutically acceptable salt, solvate or ester thereof and at least one pharmaceutically acceptable excipient. The tetracycline may be any of the tetracyclines defined herein.

The formulation may comprise a unit dosage of dibromopropamidine or diminazene and a unit dosage of a tetracycline as defined herein.

In an embodiment, the formulation comprises a unit dosage of dibromopropamidine, or a pharmaceutically acceptable salt or solvate thereof, and a unit dosage of minocycline, or a pharmaceutically acceptable salt, solvate or ester thereof.

The invention also provides two separate formulations to be used together, the formulations being;

a first formulation comprising an amidine selected from dibromopropamidine, diminazene or a pharmaceutically acceptable salt or solvate thereof, and at least one pharmaceutically acceptable excipient;

a second formulation comprising a tetracycline as defined herein, and at least one pharmaceutically acceptable excipient. The formulations may be in the form of a kit. The formulations (i.e. the kit comprising said formulations) will typically be for treating an infection or disease caused by Gram-negative or Gram-positive bacteria as defined herein Combination Therapy The present inventors have found that there is synergy in combining certain amidine compounds with tetracyclines.

The inventors have surprisingly found that the combination of an amidine compound selected from dibromopropamidine and diminazene with a tetracycline (for example the tetracycline compounds of the combination products defined herein may exhibit a synergistic effect in the inhibition of bacteria, for example *Pseudomonas aeruginosa*. The synergistic effect provided by the combination product of the invention may allow smaller dosages of each active agent to be administered to patients, thereby reducing the risk of side effects associated with the therapy. Additionally, the combination product may overcome resistance mechanisms of the treated pathogens. The combination product may have particular activity against bacterial strains in a biofilm state. The combination product may reduce the rate at which resistance evolves towards the treatment.

The combination treatments disclosed herein comprising dibromopropamidine or diminazene ("the amidine") and a tetracycline show enhanced potency against certain bacteria when administered in combination than is the case when either agent is administered alone. The term 'in combination' or 'together' in the context of the present invention refers to the administration of the two agents to the same subject during a treatment period. The amidine and the tetracycline may be administered to a subject separately, for example as two separate doses or may be in the same dose. Alternatively, the amidine may be administered to a subject substantially simultaneously, for example as a combined dosage form comprising both actives or as two or more separate dosage forms which are administered to the subject substantially simultaneously. Administration may take place concurrently or in sequence either immediately one after the other or with a time interval in between the administration of the two agents. The term 'alone' in the context of this discussion thus means administration of only one active agent and no administration of the other agent during the treatment period, even after a time interval.

Combination treatment according to the invention embraces the co-administration or sequential administration of the two active agents in a manner which enhances the overall therapeutic result relative to the administration of one of the active agents alone during the overall treatment period. The pharmaceutical formulation(s) employed for the purpose of the combination treatment may provide each active individually, i.e. separate formulations, or provide both actives in a single formulation. The, or each, formulation may be in a liquid form, either diluted or ready for dilution, or may be in a solid form. Solid forms may be provided for dissolution in a suitable solvent medium. Solid forms may also be presented in concentrated unit dosage form as tablets, capsules, lozenges etc.

In an embodiment, the active ingredients may be physically combined to allow them to be administered simultaneously. Alternatively, the combination product may allow the actives to be administered sequentially. 'Simultaneous' is intended to mean "substantially simultaneous" e.g. less than 30 mins apart, for example less than 10 minutes apart, less than 5 minutes apart or less than 1 minute apart. 'Sequential' means, for example administration of one active agent followed by administration of a further active agent more than 30 mins apart. The amidine and tetracycline of the combination product as disclosed herein may be administered by any suitable route of administration, which may be the same or different for each active agent of the combination product as disclosed herein. For example, the amidine and the tetracycline may, independently, be administered to a subject orally, parenterally, topically or by inhalation.

Patient Class

The combination product of the invention may be administered to a human or mammal suffering from a disease caused by Gram-negative bacteria, for example *Pseudomonas aeruginosa* or *Escherichia coli*. Alternatively, the human or mammal may be suffering from a disease caused by Gram-positive bacteria. When a subject is presented with an infection or disease, a clinician or veterinarian may carry out tests to establish the nature of the bacteria which is causing the infection to establish the appropriate treatment of the subject in accordance with current clinical guidelines for the use of antibiotics. Identification of the pathogen which has caused the infection or disease may enable the clinician veterinarian to select a particular amidine and/or a particular tetracycline to provide the combination treatment according to the present invention.

According to an embodiment there is provided a method for the treatment of a bacterial infection or disease in a subject, the method comprising testing a biological sample obtained from the subject to identify the bacteria causing the infection or disease and administering to the subject a therapeutically effective amount of a combination product as described herein. Testing the sample obtained from a subject to identify an infection may be carried out using well known use microbiologic laboratory methods, for example cell culture, microscopy, serological testing and/or genetic testing.

The combination product of the invention may be used in the treatment or prophylaxis of a patient at risk of developing an infection caused by any of the Gram-negative or Gram-positive bacteria disclosed herein. The combination product of the invention may be used in the treatment or prophylaxis of a patient at risk of developing an infection caused by *Pseudomonas aeruginosa*. The patient may also be at risk of developing an infection caused by *Staphylococcus aureus* and *S. epidermidis*; various species of the genus *Streptococcus*, including *S. pyogenes* and *S. pneumoniae*; *Escherichia coli*; various species of *Klebsiella*, including *K. pneumoniae*; various species of *Enterobacter*, *Enterococcus* and Acenitobacter. Such patients include but are not limited to immunocompromised individuals, cystic fibrosis patients, neutropenic patients, patients with diabetic ulcers, premature infants, burns victims and patients with wound infections.

Dosage Regimens

The application regimen used for the combination product will depend on a number of factors that may readily be determined by a clinician or veterinarian, such as the severity of the condition and its responsiveness to initial treatment, but will normally involve one or more doses of the combination product per day on an ongoing basis. The effective dosage of the amidine and the tetracycline of the combination product as disclosed herein will be determined by, for example the formulation, administration pathway, age, weight and gender of animal or human with the disease or infection.

Generally, in the combination products disclosed herein, the amount of the amidine to be administered may be in the range of 0.1 mg to 1000 mg per day, for example between 1-250 mg per day and the amount of tetracycline to be administered is will the range of 0.1 mg to 1000 mg per day, for example between 1-250 mg per day.

BRIEF DESCRIPTION OF DRAWINGS

FIG. 1 shows the plate schematic for synergy determination for the combination of tetracycline antibiotics with diminazene/dibromopropamidine.

DETAILED DESCRIPTION

Minimum Inhibitory Concentration (MIC)

In microbiology, minimum inhibitory concentration (MIC) is the lowest concentration of an antibacterial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. The MIC can be determined using standard methods, for example as described in Andrews, J. Antimicrobial Chemotherapy, 48, 2001, Suppl. S1, 5-16. Typically, MIC is determined using 96-well plates, and serial two-fold dilutions of the antibacterial agent in a culture medium containing the bacteria with an approximate concentration of $10^3$ cells per well. Plates are incubated at 37° C. for 18 to 24 hours. Optical density, at a wavelength of 600 nm, is then measured at the start and at the end of the incubation period. Inhibition in a particular well is calculated as (Inhibition=1–$OD_{test}/OD_{no\ treatment}$). The MIC value is the minimum concentration of antibacterial agent which gives 100% inhibition. Experiments are generally performed at least as triplicate biological replicates.

Combination Index (CI)

The present inventors have found that the combination products described herein provide a synergistic effect against certain bacteria.

The synergistic effect of a drug combination may be calculated using the "Chou-Talalay Method" to derive a Combination Index (CI). The method referred to herein as "CI" or "combination index" is a quantitative analysis based on a theorem proposed by Chou-Talalay in the 1980s (Chou T C, Talalay P A. J. Biol. Chem. (1977) 252: 6438-42; Chou T C. Talalay P A. Eur. J. Biochem. (1981) 115:207-216). Experimental designs and analysis of these experiments for identifying the existence of synergistic effects of a drug combination is provided in Greco et al (Pharmacological Reviews, 1995; 47(2):331-385).

The CI is measured by first calculating the fractional inhibitory concentration (FIC) of the individual actives (e.g. "compound A" or "compound B") in a combination product against a certain bacterial strain. This is calculated by dividing the minimum inhibitory concentration (MIC) of the active in a combination product by the minimum inhibitory concentration of the active alone.

$$FIC_{Compound\ A} = \frac{MIC\ of\ compound\ A\ in\ combination\ with\ compound\ B}{MIC\ of\ compound\ A\ alone}$$

$$FIC_{Compound\ B} = \frac{MIC\ of\ compound\ B\ in\ combination\ with\ compound\ A}{MIC\ of\ compound\ B\ alone}$$

The Combination Index (CI) is calculated by adding the FIC of the two actives together.

$$CI\ value = FIC_{Compound\ A} + FIC_{Compound\ B}$$

A CI value of 1 means the combined effect of the two agents is additive. A CI value of less than 1 means that the two agents act synergistically. It is therefore understood that the lower the CI value, the better the synergistic effect of the combination product. For a drug combination to show synergistic effects, the CI value will typically be less than 1.

In an embodiment, the CI value of the combination products disclosed herein will be less than 1, 0.75 or less, or preferably 0.5 or less, even more preferably the CI value will be 0.4 or less.

Definitions

Given below are definitions of terms used in this application. Any term not defined herein takes the normal meaning as the skilled person would understand the term.

Throughout the current specification, any reference to dibromopropamidine encompasses pharmaceutically acceptable salts or solvates thereof, including dibromopropamidine dihydrochloride.

Throughout the current specification, any reference to diminazene also encompasses pharmaceutically acceptable salts or solvates thereof, including diminazene aceturate.

Throughout the current specification, any reference to a combination product refers to any of the combination products disclosed herein.

In the context of the present invention, treatment of a condition encompasses both therapeutic and prophylactic treatment, of either an infectious or a non-infectious condition, in a mammal such as a human or animal, but in particular a human. It may involve complete or partial eradication of the condition, removal or amelioration of associated symptoms, arresting subsequent development of the condition, and/or prevention of, or reduction of risk of, subsequent occurrence of the condition.

The term "halo" refers to one of the halogens, group 17 of the periodic table. In particular, the term refers to fluorine, chlorine, bromine and iodine.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. For example, the term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. In preferred embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 4-7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, aryloxy, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaryl moiety. Cycloalkyls can be further substituted, e.g., with the substituents described above. An "alkylaryl" moiety is an alkyl substituted with an aryl (e.g., phenylmethyl (benzyl)).

The term "haloalkyl" refers to a hydrocarbon chain substituted with at least one halogen atom independently chosen at each occurrence, for example fluorine, chlorine, bromine and iodine. For example, the term "$C_{1-6}$ haloalkyl" refers to a linear or branched hydrocarbon chain containing 1, 2, 3, 4, 5 or 6 carbon atoms substituted with at least one halogen. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "heteroalkyl" refers to a branched or linear hydrocarbon chain containing at least one heteroatom selected from N, O and S positioned between any carbon in the chain or at an end of the chain. For example, the term "$C_{1-6}$ heteroalkyl" refers to a branched or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "alkenyl" refers to a branched or linear hydrocarbon chain containing at least one double bond. For example, the term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "alkynyl" refers to a branched or linear hydrocarbon chain containing at least one triple bond. For example, the term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The terms "alkoxy" or "lower alkoxy" refer to such alkyl groups as defined above attached to an oxygen or sulfur respectively. For example, the term "$C_{1-6}$ alkoxy" refers to a group where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described above in relation to the definition of alkyl groups. For example, substituents for the alkyl group of an alkoxy may be halogen (e.g. fluorine, chlorine, bromine and iodine), OH or $C_{1-6}$ alkoxy.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "alkylthio" refers to the group R'S— wherein R' is alkyl as defined above.

The term "alkylsulfonyl" refers to the R'SO$_2$— group wherein R' is alkyl as defined above.

The term "alkylsulfinyl" refers to the R'S(O)— group wherein R' is alkyl as defined above.

The term "amino" means the primary, secondary or tertiary amino group —NR'R"; wherein R' and R" are independently H or alkyl groups as defined above.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" refers to a ring system comprising at least one aromatic ring with at least one heteroatom within a single ring or within a fused ring system, selected from O, N and S. The ring or ring system has 4n+2 electrons in a conjugated π system where all atoms contributing to the conjugated π system are in the same plane. Examples of heteriaryls include for example, pyrrole, furan, thiophene, imidazole, benzimidazole, benzoxazole, benzothiazole, triazole, tetrazole, pyrazole, pyridine, pyrazine, pyridazine and pyrimidine, and the like.

Aryl and heteroaryl rings groups can also be fused or bridged with alicyclic or heterocyclic rings which are not aromatic so as to form a polycycle (e.g. tetralin).

The rings of an aryl or heteroaryl can be substituted at one or more ring positions with such substituents as described herein, for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety The term "heterocyclic" refers to a ring or ring system comprising at least one non-aromatic saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties and heterocycloalkenyl moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "heterocycloalkyl" refers to a saturated hydrocarbon ring system containing carbon atoms and at least one heteroatom within the ring selected from N, O and S. For example, there may be 1, 2 or 3 heteroatoms, optionally 1 or 2. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be a "C$_{3-8}$ heterocycloalkyl". The term "C$_{3-8}$ heterocycloalkyl" refers to a saturated hydrocarbon ring system containing 3, 4, 5, 6, 7 or 8 atoms at least one of the atoms being a heteroatom within the ring selected from N, O and S. The "heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. The term "bicyclic ring" includes rings where 2 atoms share more than one ring. Examples of bicyclic rings include bicyclbutane, camphene, decalin, and phthalimide. Each of the rings of the polycycle can be substituted with such substituents as described herein, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "carbonyl" includes moieties which contain a carbon double bonded to an oxygen atom. The term "substituted carbonyl" includes groups wherein the carbon of the carbonyl group is further bonded to another carbon or a heteroatom. Examples of substituents include, but are not limited to, alkyl, alkenyl, alkynyl, aryl, halogen, hydroxyl, alkylcarbonyloxy, arylcarbonyloxy, alkoxycarbonyloxy, aryloxycarbonyloxy, alkoxy, aryloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety.

The term "thiocarbonyl" includes moieties which contain a carbon double bonded to a sulfur atom. The term "substituted thiocarbonyl" includes groups wherein the carbon of the carbonyl group is further bonded to another carbon or a heteroatom. Examples of substituents include, but are not limited to, alkyl, alkenyl, alkynyl, aryl, halogen, hydroxyl, alkylcarbonyloxy, arylcarbonyloxy, alkoxycarbonyloxy, aryloxycarbonyloxy, alkoxy, aryloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety.

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

Alkanoyl groups include alkyl groups having 1 to about 4 or 5 carbonyl groups. Aroyl groups include groups having one or more carbonyl groups as a substituent to an aryl group (such as phenyl). Suitable alkaroyl groups have one or more alkylcarbonyl groups as a substituent to an aryl group such as phenylacetyl and the like. Suitable aryloyl groups are aryl or heteroaryl groups that are substituted with one or more carbonyl groups, typically 1 or 2 carbonyl groups.

The term "amino acid" or "amino acid residue" refer to an amino acid or an amino acid residue consisting of the 20 naturally occurring amino acids, i.e. alanine (Ala or A), cysteine (Cys or C), aspartic acid (Asp or D), glutamic acid (Glu or E), phenylalanine (Phe or F), glycine (Gly or G), histidine (His or H), isoleucine (lie or I), lysine (Lys or K), leucine (Leu or L), methionine (Met or M), asparagine (Asn or N), proline (Pro or P), glutamine (Gin or Q), arginine (Arg or R), serine (Ser or S), threonine (Thr or T), valine (Val or V), tryptophan (Trp or W), and tyrosine (Tyr or Y) residues. A particularly preferred amino acid residue is lysine.

The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, minocycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (for a review, see W. Rogalski, "Chemical Modifications of Tetracyclines," the entire contents of which are hereby incorporated herein by reference). Table 2 depicts tetracycline and several known other tetracycline derivatives. Throughout this specification, reference to a "tetracycline anti-bacterial agent" is intended to include "a tetracycline compound" and vice versa.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group. Prodrugs may be metabolized in vivo by esterases or by other mechanisms to hydroxyl groups or other advantageous groups. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrugs include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

The structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

It is to be understood that certain compounds described herein may exhibit the phenomenon of tautomerism. It is to be understood that the present invention includes in its definition any such tautomeric form, or a mixture thereof and is not to be limited merely to any one tautomeric form utilised within the formulae drawings or named in the Examples.

The compounds of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic, valeric acids and acid addition salts of an amino acid or derivative thereof, for example aceturate (N-acetylglycinate) salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate, hemioxalate and hemicalcium salts. Hyclate e.g. in doxycycline hyclate, is the USAN-approved contraction for monohydrochloride hemiethanolate hemihydrate. Suitable pharmaceutically acceptable salts are also disclosed in "Handbook of Pharmaceutical Salts: Properties, Selection, and Use" by Stahl and Wermuth (Wiley-VCH, Weinheim, Germany, 2002).

Pharmaceutically acceptable salts of compounds disclosed herein may be prepared by one or more of three methods:

by reacting the compound of the invention with the desired acid or base;

by removing an acid- or base-labile protecting group from a suitable precursor of the compound of the invention or by ring-opening a suitable cyclic precursor, for example, a lactone or lactam, using the desired acid or base; or by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds disclosed herein may exist in both unsolvated and solvated forms. The term 'solvate' is used herein to describe a molecular complex comprising the compound of the invention and a stoichiometric amount of one or more pharmaceutically acceptable solvent molecules, for example, ethanol or water. The term 'hydrate' may also be employed when said solvent is water.

Reference herein to a compound "or a pharmaceutically acceptable salt, solvate or ester thereof" is intended to cover pharmaceutically acceptable salts, solvates or esters of the compound as well as solvates of a salt or solvates of an ester of the compound. Similarly reference to a compound "or a pharmaceutically acceptable salt or solvate thereof" is intended to encompass the salt or solvate of the compound as well as solvates of a salt of the compound.

The compounds disclosed herein may exist in a single crystal form or in a mixture of crystal forms or they may be amorphous. Thus, compounds described herein intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The present invention also includes all pharmaceutically acceptable isotopically-labelled compounds of the invention wherein one or more atoms are replaced by atoms having the same atomic number, but an atomic mass or mass number different from the atomic mass or mass number most commonly found in nature.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

The invention is further illustrated by the following examples.

Example 1—Synergistic Effect Between Dibromopropamidine and Four Tetracycline Antibiotics Study Objective The goal of this study is to measure the synergistic effect of various tetracyclines in combination with diminazene aceturate or dibromopropamidine dihydrochloride against *Pseudomonas aeruginosa*.

Methods

Microorganisms

This study was conducted with the following strains: *Pseudomonas aeruginosa* (X11045). *P. aeruginosa* (X11045) was received form Statens Serum Institute.

Culture Medium

The bacteria from cryopreserved stocks were grown on LB agar plates [G. Bertani, "Studies on lysogenesis. I. The mode of phage liberation by lysogenic *Escherichia coli*," J. Bacteriol., vol. 62, no. 3, pp. 293-300, September 1951] and incubated overnight at 37° C.

One colony was transferred into 15 ml of cation-adjust Mueller Hinton broth (MH2) [J. H. Mueller and J. Hinton, "A Protein-Free Medium for Primary Isolation of the Gonococcus and Meningococcus," Exp. Biol. Med., vol. 48, no. 1, pp. 330-333, October 1941] and incubated overnight at 37° C. shaken at 200 rpm.

Compounds Tested

The tetracyclines and amidine compounds that were tested are shown in Table 1.

TABLE 1

Tetracycline and amidine compounds tested in combination.

| Drugs used | Chemical structure | | Molecular Weight | Protein binding (%) |
|---|---|---|---|---|
| Doxycycline hyclate | [chemical structure of doxycycline] | ·HCl<br>·½H$_2$O<br>·½CH$_3$CH$_2$OH | 512.94 | 85 |

TABLE 1-continued

Tetracycline and amidine compounds tested in combination.

| Drugs used | Chemical structure | Molecular Weight | Protein binding (%) |
|---|---|---|---|
| Minocycline hydrochloride | 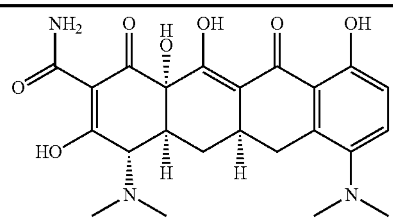 | 493.94 | 66 |
| Tetracycline hydrochloride | 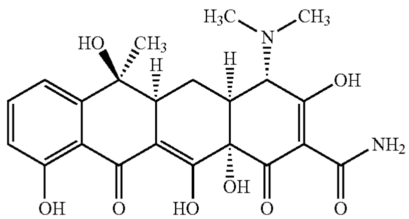 | 480.90 | 60 |
| Tigecycline hydrate | 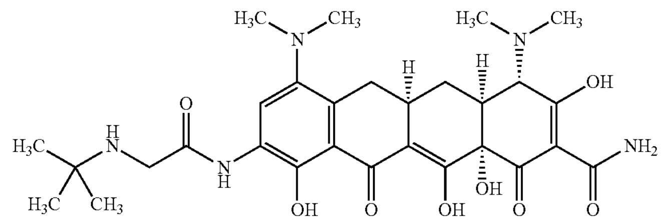 | 585.65 (as anhydrous) | 80 |
| Diminazene aceturate | 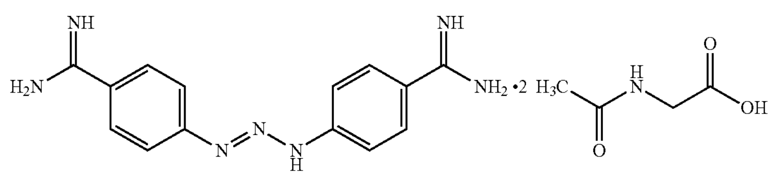 | 515.52 | 65-85 |
| Dibromopropamidine dihydrochloride | 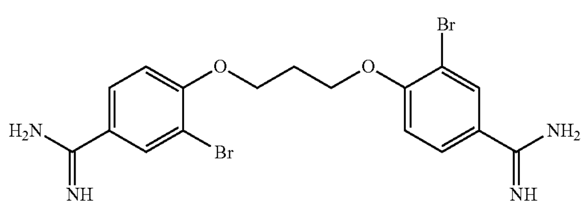 | 543.08 | |

Checkerboard Methods of Antimicrobial Combinations Synergy Determination

1. Day 1.
   Bacterial strains are isolated on agar plates and incubated overnight at 37° C. *Pseudomonas aeruginosa* (X11045) on LB agar.
2. Day 2.
   For each strain, one colony is transferred into 15 ml of Mueller Hinton broth (MHB) and incubated overnight at 37° C. shaken at 200 rpm.
3. Day 3.
   Fifty microliters of the O/N culture are inoculated to 5 ml of Mueller Hinton broth in 15 ml conical tubes and incubated for 5 hours at 37° C. shaken at 200 rpm.
4. Dispense 150 µl of MHB in each well of the $12^{th}$ column for positive and negative controls as shown above.
5. Prepare each drug to $C_{max} \times 2$
   a. Diminazene/Dibromopropamidine:
      Make a series of 2-fold dilution as shown in the plate layout. Using the 12 channel pipet, dispense 75 µl of diminazene solution in each well so that the final volume will be 150 µl and the final concentration is as shown in the plate schematic above.
   b. Tetracycline antibiotics:
      Make a series of 2-fold dilution as shown in the plate layout. Using the 8 channel pipet, dispense 75 µl of tetracycline antibiotic solution in each well so that the final volume will be 150 µl and the final concentration is as shown in the plate schematic above.

6. Inoculate each well with 1 µl of bacterial suspension
7. Incubate overnight at 37° C.
8. Day 4.

The $OD_{600}$ is measured after 18 hours incubation.

Results and Discussion

The FIC and CI values of combinations tested against *Pseudomonas aeruginosa* are shown in Tables 2 and 3.

TABLE 2

Combination of diminazene and tetracycline antibiotics against *Pseudomonas aeruginosa*.

| | MIC tetracycline (µg/ml) (combination) | MIC tetracycline (µg/ml) | FIC tetracycline | MIC diminazene (µg/ml) (combination) | MIC diminazene (µg/ml) | FIC dibromopropamidine | CI value |
|---|---|---|---|---|---|---|---|
| Doxycycline hyclate | 3.13 | 25.00 | 0.13 | 31.25 | 250.00 | 0.13 | 0.25 |
| Minocycline hydrochloride | 3.13 | 25.00 | 0.13 | 31.25 | 250.00 | 0.13 | 0.25 |
| Tetracycline hydrochloride | 4.00 | 16.00 | 0.25 | 62.50 | 250.00 | 0.25 | 0.50 |

Table 2 shows that these is strong synergy between diminazene and the tetracyclines doxycycline hyclate, minocycline hydrochloride and tetracycline hydrochloride.

TABLE 3

Combination of dibromopropamidine and four tetracycline antibiotics against *Pseudomonas aeruginosa*.

| | MIC tetracycline (µg/ml) (combination) | MIC tetracycline compound (µg/ml) | FIC tetracycline compound | MIC dibromopropamidine (µg/ml) (combination) | MIC dibromopropamidine (µg/ml) | FIC dibromopropamidine | CI value |
|---|---|---|---|---|---|---|---|
| Doxycycline hyclate | 0.50 | 16.00 | 0.03 | 2.50 | 10.00 | 0.25 | 0.28 |
| Minocycline hydrochloride | 0.50 | 16.00 | 0.03 | 2.50 | 10.00 | 0.25 | 0.28 |
| Tetracycline hydrochloride | 2.00 | 16.00 | 0.13 | 5.00 | 10.00 | 0.50 | 0.63 |
| Tigecycline hydrate | 0.50 | 32.0 | 0.02 | 5.00 | 10.00 | 0.50 | 0.52 |

It can be seen from Table 3 that the MIC for the combination products is significantly lower than the MIC for the individual compounds. Synergy can be seen with the combinations of dibromopropamidine and the four tetracyclines tested in the inhibition of *Pseudomonas aeruginosa*, with CI values between 0.28 and 0.63. Especially strong synergy is observed between dibromopropamidine combined with doxycycline and dibromopropamidine combined with minocycline.

TABLE 4

Combination of diminazene and tetracycline antibiotics against *E. Coli*.

| | MIC tetracycline (µg/ml) (combination) | MIC tetracycline compound (µg/ml) | FIC tetracycline compound | MIC diminazene (µg/ml) (combination) | MIC diminazene (µg/ml) | FIC diminazene | CI value |
|---|---|---|---|---|---|---|---|
| Doxycycline hyclate | 0.25 | 0.50 | 0.50 | 1.25 | 20.00 | 0.06 | 0.56 |
| Minocycline hydrochloride | 0.13 | 0.50 | 0.25 | 5.00 | 20.00 | 0.25 | 0.50 |
| Tetracycline hydrochloride | 0.50 | 0.50 | 1.00 | 20.00 | 20.00 | 1.00 | 2.00 |
| Tigecycline hydrate | 0.25 | 1.00 | 0.25 | 2.50 | 20.00 | 0.13 | 0.38 |

Table 4 shows that there is particularly good synergy between tigecycline and diminazene against *E. coli* compared to the other tetracycline compounds tested.

The invention claimed is:

1. A method of treating an infection or disease caused by bacteria in a subject, the method comprising administering to the subject a therapeutically effective amount of a combination product comprising;
   (i) an amidine selected from dibromopropamidine and diminazene or a pharmaceutically acceptable salt or solvate thereof; and
   (ii) a tetracycline anti-bacterial agent selected from tigecycline, doxycycline, minocycline and tetracycline, or a pharmaceutically acceptable salt, solvate or ester thereof;
   wherein the infection or disease is a dermatological condition of the skin, hair or nails, selected from infected acute and chronic dermatitis, skin and soft tissue infections, diabetic ulcers, dermatitis including atopic dermatitis, acne, impetigo and rosacea, chronic rhinosinusitis, decolonization of MRSA, pre-surgical decolonization and decolonization of dialysis patients; preferably the infection or disease is a diabetic ulcer.

2. The method of claim 1, wherein the amidine is dibromopropamidine, or a pharmaceutically acceptable salt or solvate thereof, and the tetracycline anti-bacterial agent is selected from tigecycline, doxycycline, minocycline and tetracycline, or a pharmaceutically acceptable salt, solvate or ester thereof.

3. The method of claim 1, wherein the amidine is dibromopropamidine, or a pharmaceutically acceptable salt or solvate thereof, and the tetracycline anti-bacterial agent is selected from doxycycline hyclate, minocycline hydrochloride, tetracycline hydrochloride and tigecycline hydrate.

4. The method of claim 1, wherein the amidine is diminazene, or a pharmaceutically acceptable salt or solvate thereof, and the tetracycline anti-bacterial agent is selected from doxycycline, minocycline and tetracycline or a pharmaceutically acceptable salt, solvate or ester thereof.

5. The method of claim 1, wherein the infection or disease is caused by Gram-negative bacteria.

6. The method of claim 5, wherein the infection or disease is caused by Gram-negative bacteria selected from Gram-negative bacteria selected from *Pseudomonas aeruginosa, Pseudomonas fluorescens, Pseudomonas acidovorans, Pseudomonas alcaligenes, Pseudomonas putida, Stenotrophomonas maltophilia, Achromobacter xylosoxidans, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morgana, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* and *Bacteroides splanchnicus.*

7. The method of claim 5, wherein the infection or disease is caused by the bacteria *Pseudomonas aeruginosa.*

8. The method of claim 5, wherein the infection or disease is caused by the bacteria *Escherichia coli.*

9. The method of claim 1, wherein the infection or disease is selected from skin and soft tissue infections; diabetic ulcers; and dermatitis including atopic dermatitis.

10. The method of claim 1, wherein the combination product is administered topically.

11. A combination product comprising diminazene, or a pharmaceutically acceptable salt or solvate thereof, and doxycycline or a pharmaceutically acceptable salt, solvate or ester thereof; with the provisio that when the diminazene is diminazene aceturate, the combination product does not comprise enrofloxacin and/or metronidazole.

12. A combination product comprising diminazene, or a pharmaceutically acceptable salt or solvate thereof, and minocycline or a pharmaceutically acceptable salt, solvate or ester thereof.

13. A combination product comprising diminazene, or a pharmaceutically acceptable salt or solvate thereof, and tetracycline or pharmaceutically acceptable salts, solvates or esters thereof.

14. A combination product comprising dibromopropamidine, or a pharmaceutically acceptable salt or solvate thereof, and minocycline, or a pharmaceutically acceptable salt, solvate or ester thereof.

15. A method of treating an infection or disease caused by bacteria in a subject, the method comprising administering to the subject a therapeutically effective amount of a combination product comprising;
   (i) an amidine selected from dibromopropamidine and diminazene or a pharmaceutically acceptable salt or solvate thereof; and
   (ii) a tetracycline anti-bacterial agent or a pharmaceutically acceptable salt, solvate or ester thereof,
      wherein the infection or disease is an ophthalmic condition selected from eye diseases, ocular infections, acute and chronic uveitis, corneal ulceration, dry eye, conjunctivitis, acute conjunctivitis, chronic conjunctivitis, inclusion conjunctivitis, keratitis, blepharitis, canaliculitis, endophthalmitis, trachoma, uveitis, and orbital or preseptal cellulitis.

\* \* \* \* \*